United States Patent
Moehle et al.

(10) Patent No.: US 12,239,311 B2
(45) Date of Patent: *Mar. 4, 2025

(54) KNOTLESS SUTURE FASTENER INSTALLATION SYSTEM

(71) Applicant: Edwards Lifesciences Corporation, Irvine, CA (US)

(72) Inventors: Ryan Moehle, Salt Lake City, UT (US); Jeremiah Morgan, South Jordan, UT (US); Carey Philip Hendsbee, San Clemente, CA (US); Kevin K. Dang, Garden Grove, CA (US); Brian R. Jacobs, Herriman, UT (US); Brent K. Hoffman, Taylorsville, UT (US); Jeffrey L. Mahoney, Busby, MT (US); Manouchehr A. Miraki, Laguna Hills, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/069,063

(22) Filed: Dec. 20, 2022

(65) Prior Publication Data

US 2023/0127317 A1  Apr. 27, 2023

Related U.S. Application Data

(63) Continuation of application No. 16/586,670, filed on Sep. 27, 2019, now Pat. No. 11,553,908, which is a
(Continued)

(51) Int. Cl.
*A61B 17/04* (2006.01)
*A61B 17/00* (2006.01)
*A61F 2/24* (2006.01)

(52) U.S. Cl.
CPC ...... *A61B 17/0401* (2013.01); *A61B 17/0487* (2013.01); *A61F 2/2409* (2013.01);
(Continued)

(58) Field of Classification Search
CPC ...... A61B 2017/0454; A61B 2017/045; A61B 2017/0451; A61B 2017/0448;
(Continued)

(56) References Cited

U.S. PATENT DOCUMENTS 2,264,679 A  12/1941 Ravel
2,516,710 A   7/1950 Mascolo
(Continued)

FOREIGN PATENT DOCUMENTS

CA   2141911   4/2002
CA   2141913   4/2002
(Continued)

*Primary Examiner* — Ashley L Fishback
(74) *Attorney, Agent, or Firm* — Klarquist Sparkman, LLP

(57) ABSTRACT

A knotless suture fastener installation system for securing medical devices such as cardiac implants. The knotless suture fasteners may be spring-biased so as to grip onto sutures passed therethrough. The system includes a fastener deployment tool with a proximal handle and a distal shaft to which a fastener cartridge attaches. A plurality of disposable cartridges are sequentially attached to the end of the deployment tool and used to secure the medical implant one fastener at a time. The deployment tool may also cut the sutures being fastened.

20 Claims, 15 Drawing Sheets

Related U.S. Application Data continuation of application No. 15/438,404, filed on Feb. 21, 2017, now Pat. No. 10,426,458, which is a continuation of application No. 14/329,797, filed on Jul. 11, 2014, now Pat. No. 9,592,048.

(60) Provisional application No. 61/845,359, filed on Jul. 11, 2013.

(52) U.S. Cl.
CPC .......... *A61F 2/2412* (2013.01); *A61F 2/2448* (2013.01); *A61B 2017/00367* (2013.01); *A61B 2017/0053* (2013.01); *A61B 2017/0409* (2013.01); *A61B 2017/0416* (2013.01); *A61B 2017/0488* (2013.01); *A61F 2220/0008* (2013.01)

(58) Field of Classification Search
CPC .... A61B 2017/0404; A61B 2017/0414; A61B 2017/0409; A61B 2017/0456
See application file for complete search history.

(56) References Cited

U.S. PATENT DOCUMENTS

| | | |
|---|---|---|
| 2,715,486 A | 8/1955 | Marcoff-Moghadam et al. |
| 2,890,519 A | 6/1959 | Storz, Jr. |
| 3,143,742 A | 8/1964 | Cromie |
| 3,249,104 A | 5/1966 | Hohnstein |
| 3,274,658 A | 9/1966 | Pile |
| 3,452,742 A | 7/1969 | Muller |
| 3,506,012 A | 4/1970 | Brown |
| 3,509,882 A | 5/1970 | Blake |
| 3,541,591 A | 11/1970 | Hoegerman |
| 3,547,103 A | 12/1970 | Cook |
| 3,570,497 A | 3/1971 | Lemole |
| 3,608,095 A | 9/1971 | Barry |
| 3,638,654 A | 2/1972 | Akuba |
| RE27,391 E | 6/1972 | Merser |
| 3,753,438 A | 8/1973 | Wood et al. |
| 3,859,668 A | 1/1975 | Anderson |
| 3,875,648 A | 4/1975 | Bone |
| 3,898,999 A | 8/1975 | Haller |
| 3,910,281 A | 10/1975 | Kletschka et al. |
| 3,954,109 A | 5/1976 | Patel |
| 3,958,576 A | 5/1976 | Komiya |
| 3,976,079 A | 8/1976 | Samuels et al. |
| 3,988,810 A | 11/1976 | Emery |
| 3,996,623 A | 12/1976 | Kaster |
| 4,038,725 A | 8/1977 | Keefe |
| 4,103,690 A | 8/1978 | Harris |
| 4,140,125 A | 2/1979 | Smith |
| 4,170,990 A | 10/1979 | Baumgart et al. |
| 4,192,315 A | 3/1980 | Hilzinger et al. |
| 4,217,902 A | 8/1980 | March |
| 4,324,248 A | 4/1982 | Perlin |
| 4,345,601 A | 8/1982 | Fukuda |
| 4,416,266 A | 11/1983 | Baucom |
| 4,456,017 A | 6/1984 | Miles |
| 4,485,816 A | 12/1984 | Krumme |
| 4,522,207 A | 6/1985 | Klieman et al. |
| 4,535,764 A | 8/1985 | Ebert |
| 4,548,202 A | 10/1985 | Duncan |
| 4,549,545 A | 10/1985 | Levy |
| 4,586,502 A | 5/1986 | Bedi et al. |
| 4,586,503 A | 5/1986 | Kirsch et al. |
| 4,595,007 A | 6/1986 | Mericle |
| 4,612,932 A | 9/1986 | Caspar et al. |
| 4,637,380 A | 1/1987 | Orejola |
| 4,665,906 A | 5/1987 | Jervis |
| 4,683,895 A | 8/1987 | Pohndorf |
| 4,705,040 A | 11/1987 | Mueller et al. |
| 4,719,924 A | 1/1988 | Crittenden et al. |
| 4,730,615 A | 3/1988 | Sutherland et al. |
| 4,741,330 A | 5/1988 | Hayhurst |
| 4,743,253 A | 5/1988 | Magladry |
| 4,750,492 A | 6/1988 | Jacobs |
| 4,809,695 A | 3/1989 | Gwathmey et al. |
| 4,823,794 A | 4/1989 | Pierce |
| 4,863,460 A | 9/1989 | Magladry |
| 4,873,975 A | 10/1989 | Walsh et al. |
| 4,896,668 A | 1/1990 | Popoff et al. |
| 4,899,744 A | 2/1990 | Fujitsuka et al. |
| 4,901,721 A | 2/1990 | Hakki |
| 4,924,866 A | 5/1990 | Yoon |
| 4,926,860 A | 5/1990 | Stice et al. |
| 4,929,240 A | 5/1990 | Kirsch et al. |
| 4,932,955 A | 6/1990 | Merz et al. |
| 4,950,283 A | 8/1990 | Dzubow et al. |
| 4,950,285 A | 8/1990 | Wilk |
| 4,955,913 A | 9/1990 | Robinson |
| 4,976,715 A | 12/1990 | Bays et al. |
| 4,983,176 A | 1/1991 | Cushman et al. |
| 4,990,152 A | 2/1991 | Yoon |
| 4,997,439 A | 3/1991 | Chen |
| 5,002,550 A | 3/1991 | Li |
| 5,002,562 A | 3/1991 | Oberlander |
| 5,002,563 A | 3/1991 | Pyka et al. |
| 5,026,379 A | 6/1991 | Yoon |
| 5,047,047 A | 9/1991 | Yoon |
| 5,053,047 A | 10/1991 | Yoon |
| 5,070,805 A | 12/1991 | Plante |
| 5,071,431 A | 12/1991 | Sauter et al. |
| 5,074,874 A | 12/1991 | Yoon et al. |
| 5,078,731 A | 1/1992 | Hayhurst |
| 5,100,418 A | 3/1992 | Yoon et al. |
| 5,116,840 A | 5/1992 | Ganguly et al. |
| 5,123,913 A | 6/1992 | Wilk et al. |
| RE34,021 E | 8/1992 | Mueller et al. |
| 5,152,769 A | 10/1992 | Baber |
| 5,154,189 A | 10/1992 | Oberlander |
| 5,158,566 A | 10/1992 | Pianetti |
| 5,163,954 A | 11/1992 | Curcio et al. |
| 5,171,250 A | 12/1992 | Yoon |
| 5,171,251 A | 12/1992 | Bregen et al. |
| 5,171,252 A | 12/1992 | Friedland |
| 5,174,087 A | 12/1992 | Bruno |
| 5,196,022 A | 3/1993 | Bilweis |
| 5,219,358 A | 6/1993 | Bendel et al. |
| 5,222,976 A | 6/1993 | Yoon |
| 5,234,449 A | 8/1993 | Bruker et al. |
| 5,236,440 A | 8/1993 | Hlavacek |
| 5,242,456 A | 9/1993 | Nash et al. |
| 5,246,443 A | 9/1993 | Mai |
| 5,258,011 A | 11/1993 | Drews |
| 5,258,015 A | 11/1993 | Li et al. |
| 5,269,783 A | 12/1993 | Sander |
| 5,269,809 A | 12/1993 | Hayhurst et al. |
| 5,282,832 A | 2/1994 | Toso et al. |
| 5,290,289 A | 3/1994 | Sanders et al. |
| 5,304,204 A | 4/1994 | Bregen |
| 5,306,290 A | 4/1994 | Martins et al. |
| 5,306,296 A | 4/1994 | Wright et al. |
| 5,312,436 A | 5/1994 | Coffey et al. |
| 5,330,503 A | 7/1994 | Yoon |
| 5,336,239 A | 8/1994 | Gimpelson |
| 5,356,424 A | 10/1994 | Buzerak et al. |
| 5,374,268 A | 12/1994 | Sander |
| 5,383,904 A | 1/1995 | Totakura et al. |
| 5,383,905 A | 1/1995 | Golds et al. |
| 5,391,173 A | 2/1995 | Wilk |
| 5,403,346 A | 4/1995 | Loeser |
| 5,409,499 A | 4/1995 | Yi |
| 5,437,680 A | 8/1995 | Yoon |
| 5,437,685 A | 8/1995 | Blasnik |
| 5,439,479 A | 8/1995 | Shichman et al. |
| 5,445,167 A | 8/1995 | Yoon et al. |
| 5,450,860 A | 9/1995 | O'Connor |
| 5,452,733 A | 9/1995 | Sterman et al. |
| 5,456,246 A | 10/1995 | Schmieding et al. |
| 5,462,558 A | 10/1995 | Kolesa et al. |
| 5,462,561 A | 10/1995 | Voda |
| 5,474,557 A | 12/1995 | Mai |

(56) References Cited

U.S. PATENT DOCUMENTS

| | | |
|---|---|---|
| 5,474,572 A | 12/1995 | Hayhurst |
| 5,480,405 A | 1/1996 | Yoon |
| 5,486,197 A | 1/1996 | Le et al. |
| 5,496,336 A | 3/1996 | Cosgrove et al. |
| 5,499,990 A | 3/1996 | Schulken et al. |
| 5,500,000 A | 3/1996 | Feagin et al. |
| 5,520,691 A | 5/1996 | Branch |
| 5,520,702 A | 5/1996 | Sauer et al. |
| 5,527,342 A | 6/1996 | Pietrzak et al. |
| 5,531,763 A | 7/1996 | Mastri et al. |
| 5,545,178 A | 8/1996 | Kensey et al. |
| 5,549,619 A | 8/1996 | Peters et al. |
| 5,562,685 A | 10/1996 | Mollenauer et al. |
| 5,569,274 A | 10/1996 | Rapacki et al. |
| 5,569,301 A | 10/1996 | Granger et al. |
| 5,582,616 A | 12/1996 | Bolduc et al. |
| 5,582,619 A | 12/1996 | Ken |
| 5,586,983 A | 12/1996 | Sanders et al. |
| 5,591,179 A | 1/1997 | Edelstein |
| 5,593,414 A | 1/1997 | Shipp et al. |
| 5,593,424 A | 1/1997 | Northrup |
| 5,609,608 A | 3/1997 | Benett et al. |
| 5,626,590 A | 5/1997 | Wilk |
| 5,630,824 A | 5/1997 | Hart |
| 5,632,752 A | 5/1997 | Buelna |
| 5,632,753 A | 5/1997 | Loeser |
| 5,643,289 A | 7/1997 | Sauer et al. |
| 5,643,295 A | 7/1997 | Yoon |
| 5,645,553 A | 7/1997 | Kolesa et al. |
| 5,645,568 A | 7/1997 | Chervitz et al. |
| 5,665,109 A | 9/1997 | Yoon |
| 5,669,917 A | 9/1997 | Sauer et al. |
| 5,669,935 A | 9/1997 | Rosenman et al. |
| 5,681,351 A | 10/1997 | Jamiolkowski et al. |
| 5,683,417 A | 11/1997 | Cooper |
| 5,695,505 A | 12/1997 | Yoon |
| 5,697,943 A | 12/1997 | Sauer et al. |
| 5,700,270 A | 12/1997 | Peyser et al. |
| 5,700,271 A | 12/1997 | Whitfield et al. |
| 5,707,380 A | 1/1998 | Hinchliffe et al. |
| 5,709,693 A | 1/1998 | Taylor |
| 5,709,695 A | 1/1998 | Northrup, III |
| 5,725,539 A | 3/1998 | Matern |
| 5,725,542 A | 3/1998 | Yoon |
| 5,725,556 A | 3/1998 | Moser et al. |
| 5,728,135 A | 3/1998 | Bregen et al. |
| 5,735,290 A | 4/1998 | Sterman et al. |
| 5,735,877 A | 4/1998 | Pagedas |
| 5,766,183 A | 6/1998 | Sauer |
| 5,776,188 A | 7/1998 | Shepherd et al. |
| 5,799,661 A | 9/1998 | Boyd et al. |
| 5,810,851 A | 9/1998 | Yoon |
| 5,810,882 A | 9/1998 | Bolduc et al. |
| 5,820,631 A | 10/1998 | Nobles |
| 5,824,008 A | 10/1998 | Bolduc et al. |
| 5,830,221 A | 11/1998 | Stein et al. |
| 5,833,696 A | 11/1998 | Whitfield et al. |
| 5,845,645 A | 12/1998 | Bonutti |
| 5,849,019 A | 12/1998 | Yoon |
| 5,861,004 A | 1/1999 | Kensey et al. |
| 5,879,371 A | 3/1999 | Gardiner et al. |
| 5,891,130 A | 4/1999 | Palermo et al. |
| 5,891,160 A | 4/1999 | Williamson, IV et al. |
| 5,895,393 A | 4/1999 | Pagedas |
| 5,895,394 A | 4/1999 | Kienzle et al. |
| 5,919,207 A | 7/1999 | Taheri |
| 5,948,001 A | 9/1999 | Larsen |
| 5,961,481 A | 10/1999 | Sterman et al. |
| 5,961,539 A | 10/1999 | Northrup et al. |
| 5,964,772 A | 10/1999 | Bolduc et al. |
| 5,972,024 A | 10/1999 | Northrup et al. |
| 5,976,159 A | 11/1999 | Bolduc et al. |
| 5,984,917 A | 11/1999 | Fleischman et al. |
| 5,989,242 A | 11/1999 | Saadat et al. |
| 5,989,268 A | 11/1999 | Pugsley, Jr. et al. |
| 5,997,556 A | 12/1999 | Tanner |
| 6,001,110 A | 12/1999 | Adams |
| 6,013,084 A | 1/2000 | Ken et al. |
| 6,015,428 A | 1/2000 | Pagedas |
| 6,039,176 A | 3/2000 | Wright |
| 6,066,160 A | 5/2000 | Colvin et al. |
| 6,074,409 A | 6/2000 | Goldfarb |
| 6,120,524 A | 9/2000 | Taheri |
| 6,132,438 A | 10/2000 | Fleischman et al. |
| 6,139,540 A | 10/2000 | Rost et al. |
| 6,143,004 A | 11/2000 | Davis et al. |
| 6,176,413 B1 | 1/2001 | Heck et al. |
| 6,190,373 B1 | 2/2001 | Palermo et al. |
| 6,193,733 B1 | 2/2001 | Adams |
| 6,193,734 B1 | 2/2001 | Bolduc et al. |
| 6,231,592 B1 | 5/2001 | Bonutti et al. |
| 6,241,765 B1 | 6/2001 | Griffin et al. |
| 6,254,615 B1 | 7/2001 | Bolduc et al. |
| 6,306,141 B1 | 10/2001 | Jervis |
| 6,346,112 B2 | 2/2002 | Adams |
| 6,368,334 B1 | 4/2002 | Sauer |
| 6,432,123 B2 | 8/2002 | Schwartz et al. |
| 6,475,230 B1 | 11/2002 | Bonutti et al. |
| 6,514,265 B2 | 2/2003 | Ho et al. |
| 6,533,796 B1 | 3/2003 | Sauer et al. |
| 6,537,290 B2 | 3/2003 | Adams et al. |
| 6,551,332 B1 | 4/2003 | Nguyen et al. |
| 6,589,279 B1 | 7/2003 | Anderson et al. |
| 6,607,541 B1 | 8/2003 | Gardiner et al. |
| 6,613,059 B2 | 9/2003 | Schaller et al. |
| 6,626,930 B1 | 9/2003 | Allen et al. |
| 6,641,592 B1 | 11/2003 | Sauer et al. |
| 6,641,593 B1 | 11/2003 | Schaller et al. |
| 6,682,540 B1 | 1/2004 | Sancoff et al. |
| 6,719,767 B1 | 4/2004 | Kimblad |
| 6,746,457 B2 | 6/2004 | Dana et al. |
| 6,749,622 B2 | 6/2004 | McGuckin, Jr. et al. |
| 6,776,784 B2 | 8/2004 | Ginn |
| 6,860,890 B2 | 3/2005 | Bachman et al. |
| 6,896,686 B2 | 5/2005 | Weber |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,945,980 B2 | 9/2005 | Nguyen et al. |
| 6,960,221 B2 | 11/2005 | Ho et al. |
| 7,011,669 B2 | 3/2006 | Kimblad |
| 7,083,628 B2 | 8/2006 | Bachman |
| 7,094,244 B2 | 8/2006 | Schreck |
| 7,112,207 B2 | 9/2006 | Allen et al. |
| 7,220,266 B2 | 5/2007 | Gambale |
| 7,235,086 B2 | 6/2007 | Sauer et al. |
| 7,264,625 B1 | 9/2007 | Buncke |
| 7,381,210 B2 | 6/2008 | Zarbatany et al. |
| 7,628,797 B2 | 12/2009 | Tieu et al. |
| 7,731,727 B2 | 6/2010 | Sauer |
| 7,833,237 B2 | 11/2010 | Sauer |
| 7,842,051 B2 | 11/2010 | Dana et al. |
| 7,862,584 B2 | 1/2011 | Lyons et al. |
| 7,875,056 B2 | 1/2011 | Jervis et al. |
| 7,959,674 B2 | 6/2011 | Shu et al. |
| 7,981,139 B2 | 7/2011 | Martin et al. |
| 8,021,421 B2 | 9/2011 | Fogarty et al. |
| 8,100,923 B2 | 1/2012 | Paraschac et al. |
| 8,105,355 B2 | 1/2012 | Page et al. |
| 8,252,005 B2 | 8/2012 | Findlay et al. |
| 8,398,657 B2 | 3/2013 | Sauer |
| 8,398,680 B2 | 3/2013 | Sauer et al. |
| 8,425,555 B2 | 4/2013 | Page et al. |
| 8,480,686 B2 | 7/2013 | Bakos et al. |
| 8,753,373 B2 | 6/2014 | Chau et al. |
| 9,017,347 B2 | 4/2015 | Oba et al. |
| 2003/0109922 A1 | 6/2003 | Peterson et al. |
| 2003/0195563 A1 | 10/2003 | Foerster |
| 2003/0233105 A1 | 12/2003 | Gayton |
| 2004/0181238 A1 | 9/2004 | Zarbatany et al. |
| 2004/0204724 A1 | 10/2004 | Kissel et al. |
| 2004/0249414 A1 | 12/2004 | Kissel et al. |
| 2005/0251209 A1 | 11/2005 | Saadat et al. |

(56) References Cited

U.S. PATENT DOCUMENTS

| | | |
|---|---|---|
| 2006/0047314 A1 | 3/2006 | Green |
| 2006/0079913 A1 | 4/2006 | Whitfield et al. |
| 2006/0089571 A1 | 4/2006 | Gertner |
| 2006/0184203 A1 | 8/2006 | Martin et al. |
| 2006/0265010 A1 | 11/2006 | Paraschac et al. |
| 2006/0276871 A1 | 12/2006 | Lamson et al. |
| 2006/0282119 A1 | 12/2006 | Perchik |
| 2007/0005079 A1 | 1/2007 | Zarbatany et al. |
| 2007/0005081 A1 | 1/2007 | Findlay et al. |
| 2007/0049952 A1 | 3/2007 | Weiss |
| 2007/0049970 A1 | 3/2007 | Belef et al. |
| 2007/0088391 A1 | 4/2007 | McAlexander et al. |
| 2007/0179530 A1 | 8/2007 | Tieu et al. |
| 2007/0270907 A1 | 11/2007 | Stokes et al. |
| 2008/0154286 A1 | 6/2008 | Abbott et al. |
| 2008/0255591 A1 | 10/2008 | Harada et al. |
| 2008/0281356 A1 | 11/2008 | Chau et al. |
| 2009/0143821 A1 | 6/2009 | Stupak |
| 2009/0281377 A1 | 11/2009 | Newell et al. |
| 2010/0001038 A1 | 1/2010 | Levin et al. |
| 2010/0076462 A1 | 3/2010 | Bakos et al. |
| 2010/0324597 A1 | 12/2010 | Shikhman |
| 2011/0087241 A1 | 4/2011 | Nguyen |
| 2011/0087242 A1 | 4/2011 | Pribanic et al. |
| 2011/0224714 A1 | 9/2011 | Gertner |
| 2011/0283514 A1 | 11/2011 | Fogarty et al. |
| 2012/0089182 A1 | 4/2012 | Page et al. |
| 2012/0102526 A1 | 4/2012 | Lejeune |
| 2013/0053884 A1 | 2/2013 | Roorda |
| 2013/0110164 A1 | 5/2013 | Milazzo et al. |
| 2013/0158600 A1 | 6/2013 | Conklin et al. |
| 2013/0165953 A1 | 6/2013 | Oba et al. |
| 2013/0231701 A1* | 9/2013 | Voss .................. A61B 17/0485 606/232 |
| 2013/0282028 A1 | 10/2013 | Conklin et al. |
| 2014/0031864 A1 | 1/2014 | Jafari et al. |

FOREIGN PATENT DOCUMENTS

| | | |
|---|---|---|
| CN | 2558335 Y | 7/2003 |
| DE | 69512446 T2 | 5/2000 |
| DE | 69612447 T2 | 7/2001 |
| EP | 0669101 A1 | 8/1995 |
| EP | 0669103 A1 | 8/1995 |
| EP | 1484023 A1 | 12/2004 |
| WO | 01049207 A2 | 7/2001 |
| WO | 0166001 A2 | 9/2001 |
| WO | 2004/024006 A1 | 3/2004 |

* cited by examiner

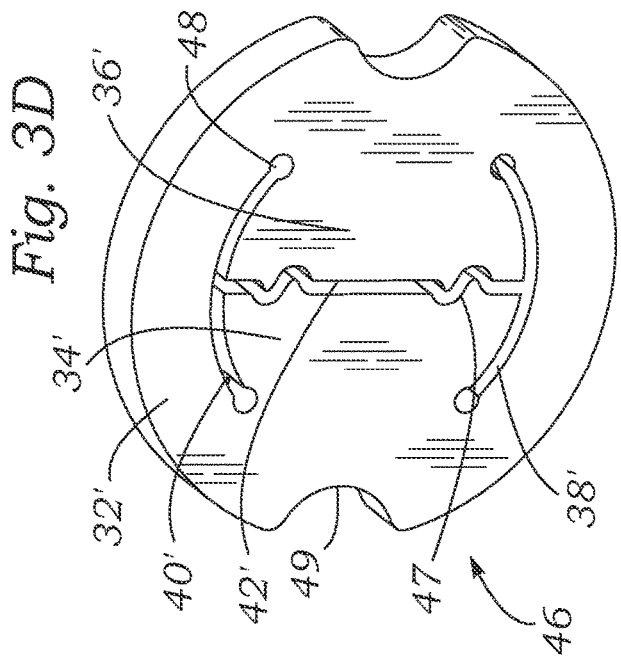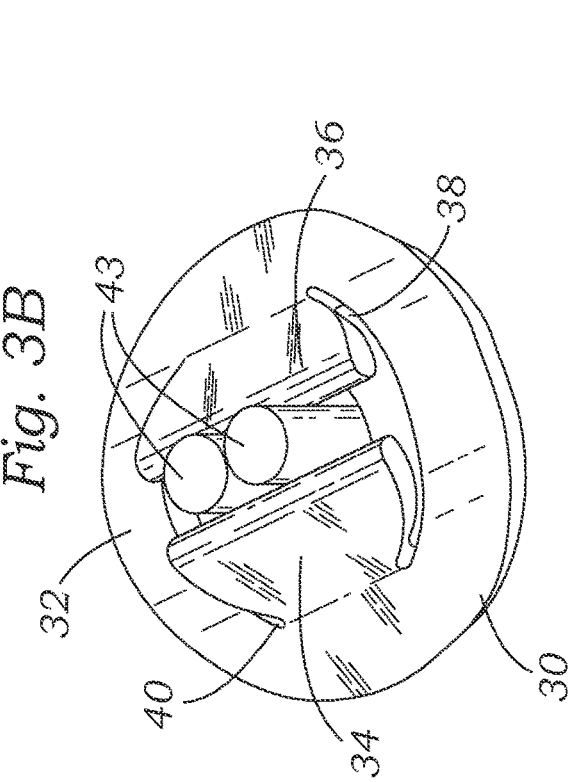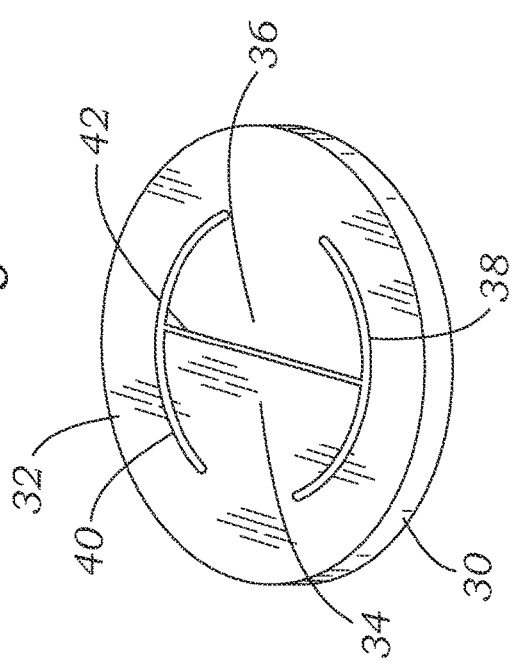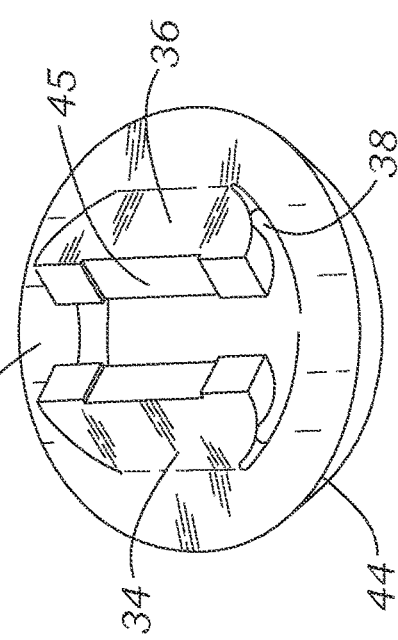

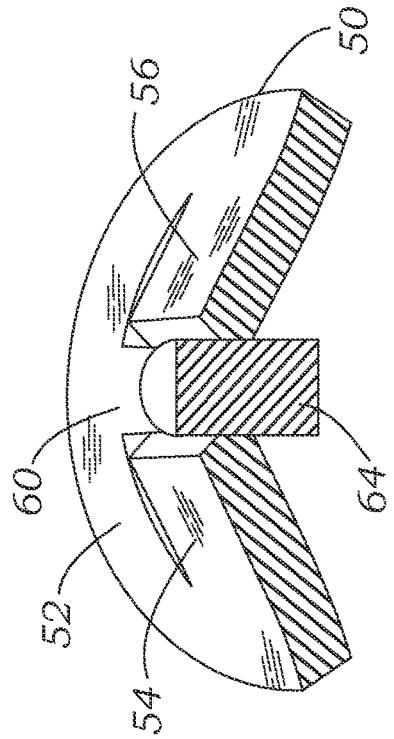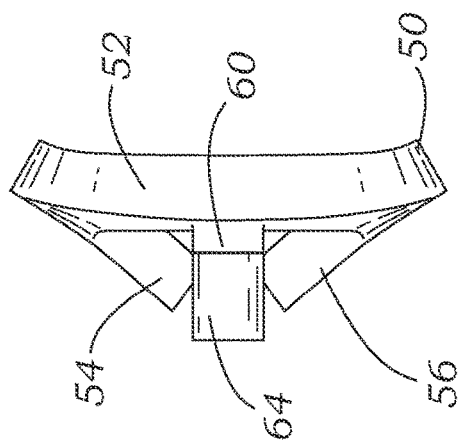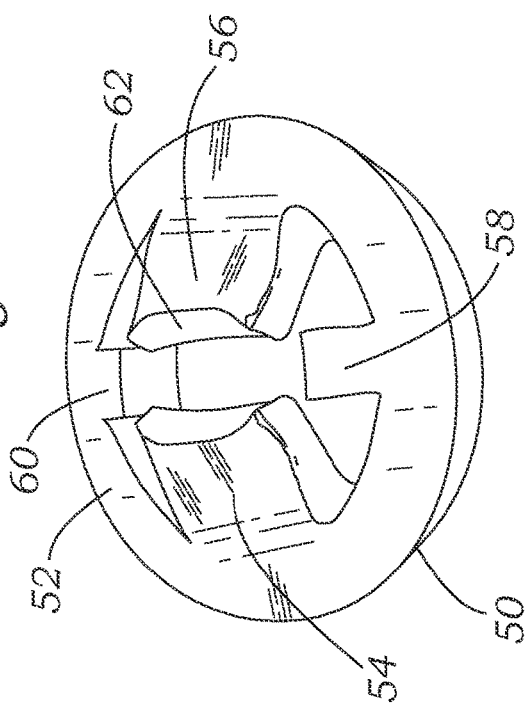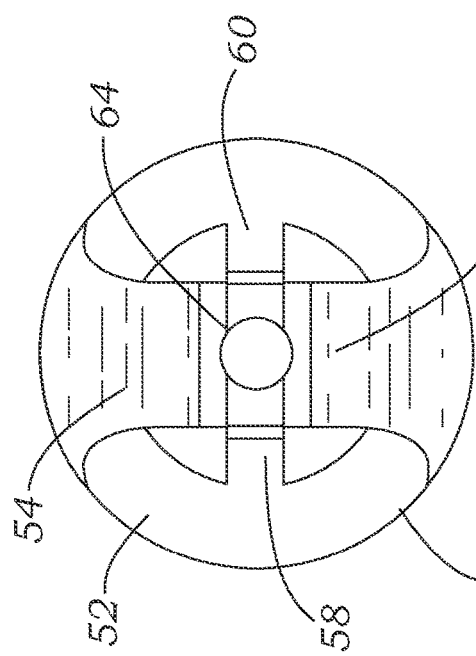

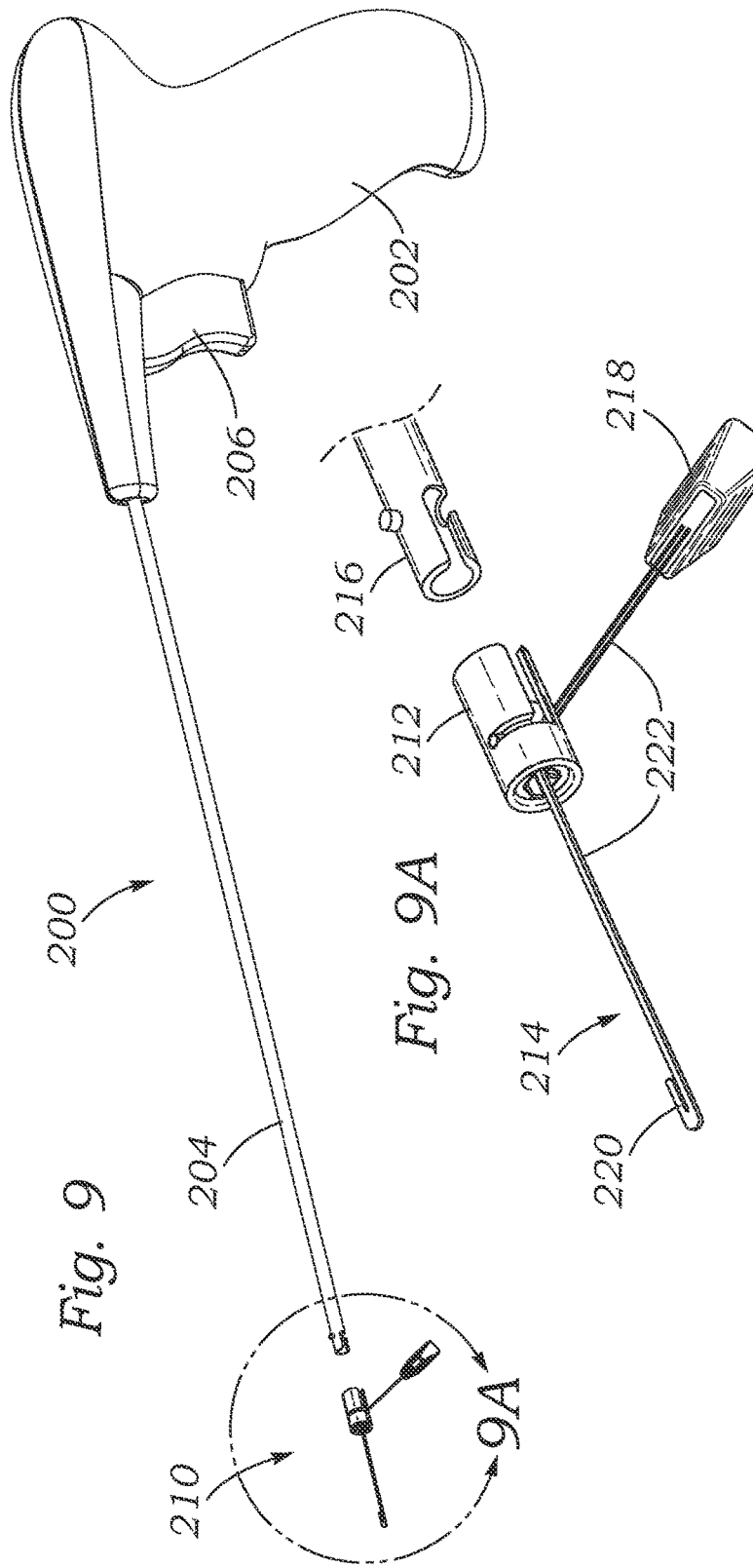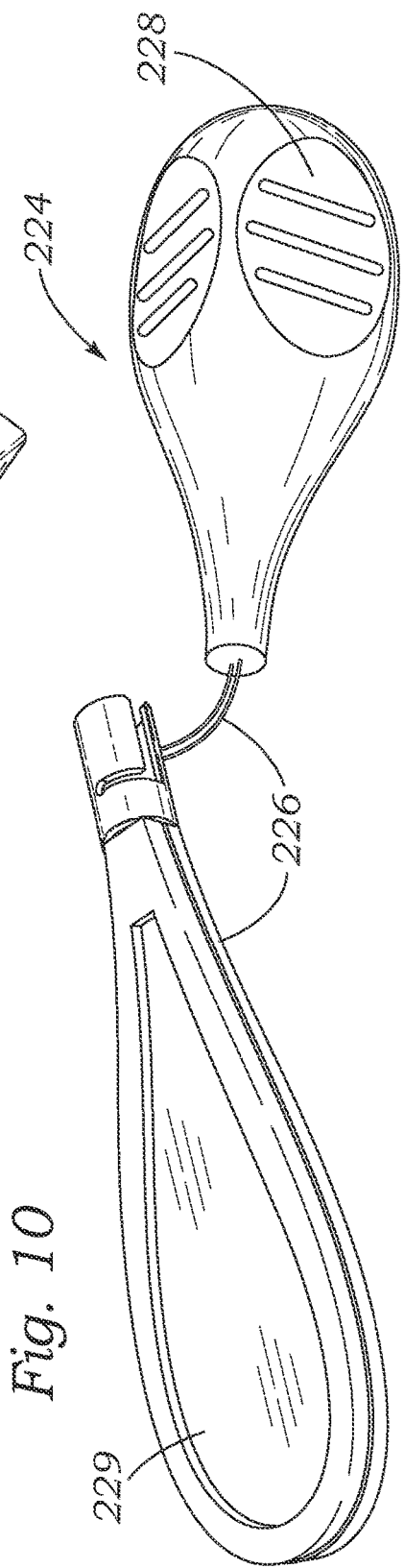

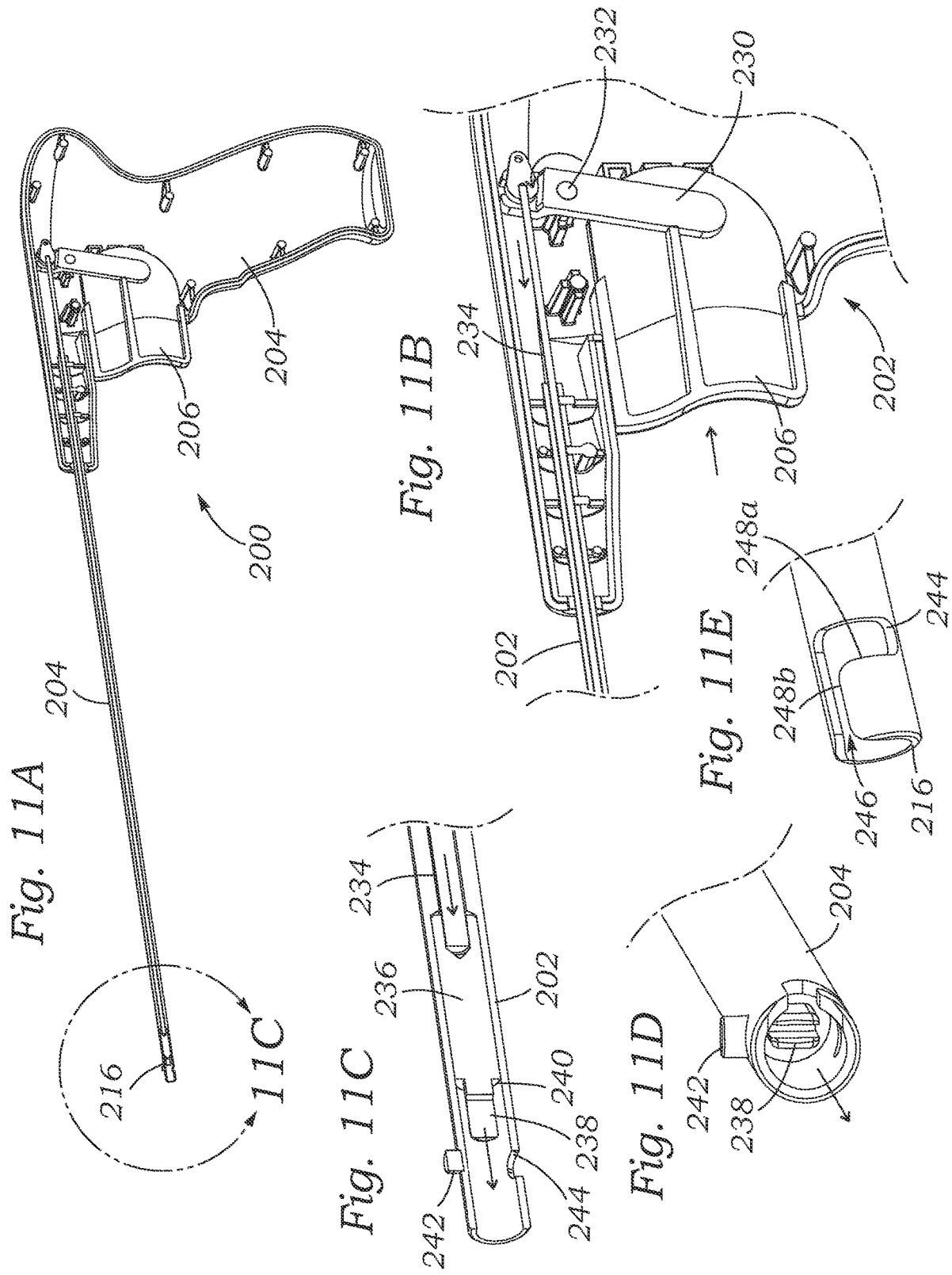

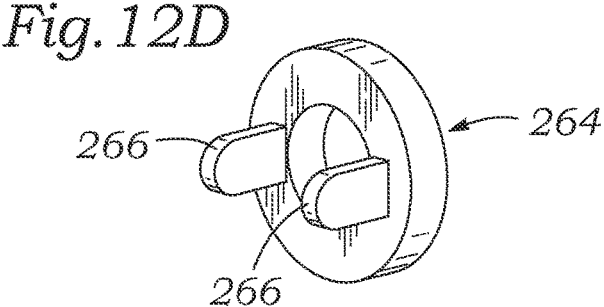
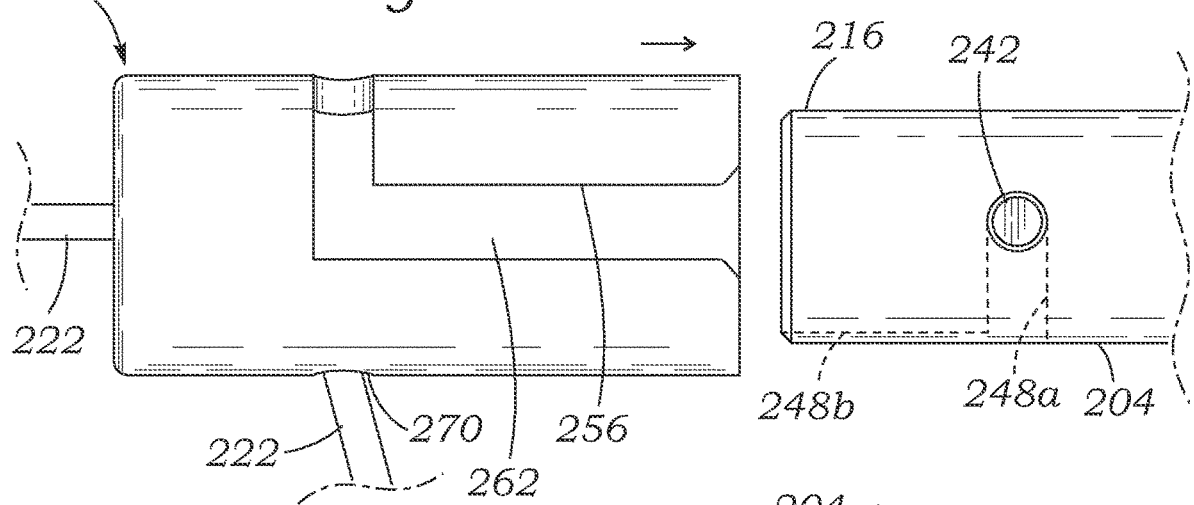
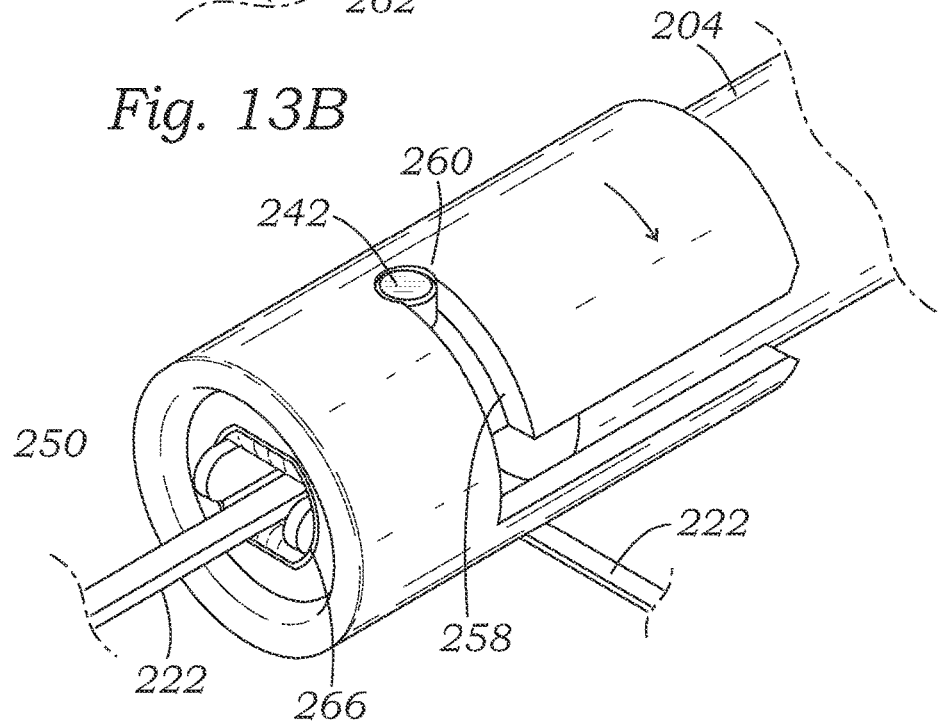

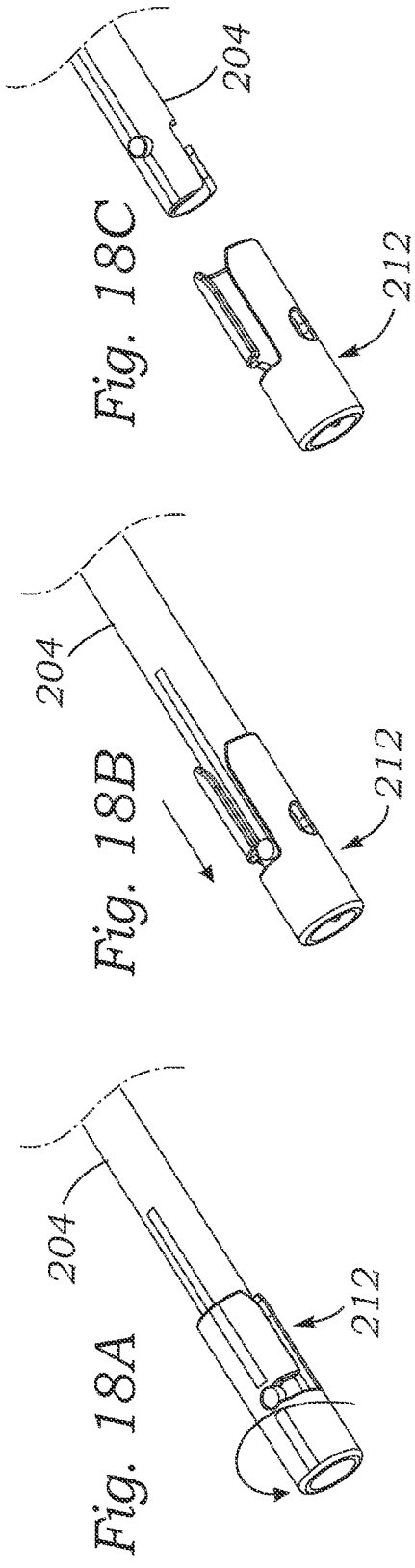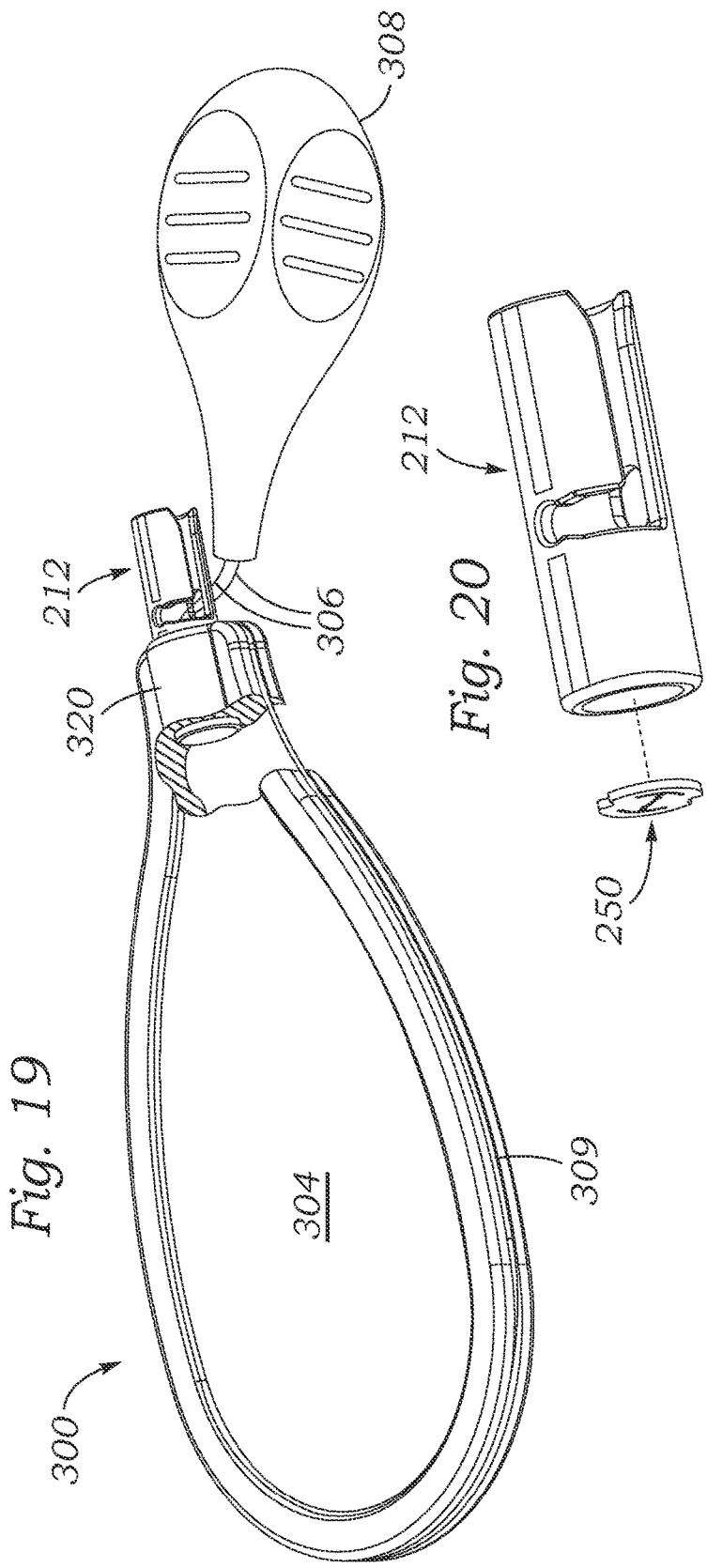

KNOTLESS SUTURE FASTENER INSTALLATION SYSTEM

CROSS-REFERENCE TO RELATED APPLICATIONS

This application is a continuation of U.S. patent application Ser. No. 16/586,670, filed Sep. 27, 2019, which is a continuation of U.S. patent application Ser. No. 15/438,404, filed Feb. 21, 2017, now U.S. Pat. No. 10,426,458, which is a continuation of U.S. patent application Ser. No. 14/329,797, filed Jul. 11, 2014, now U.S. Pat. No. 9,592,048, which claims the benefit of U.S. Patent Application No. 61/845,359, filed Jul. 11, 2013, all of which are incorporated by reference herein in their entireties.

FIELD

The present invention relates generally to a system for installing knotless suture fasteners onto sutures used, for example, to secure medical implants without requiring suture knots.

BACKGROUND

Heart valve disease is a widespread condition in which one or more of the valves of the heart fails to function properly. Various surgical techniques may be used to repair a diseased or damaged valve, including securing a cardiac implant to the diseased annulus. Cardiac implants include a prosthetic heart valves and annuloplasty rings. In a valve replacement operation, the damaged leaflets are excised and the annulus sculpted to receive a replacement valve. About one-half of patients receive a mechanical heart valve, which are composed of rigid, synthetic materials, and the remaining patients received bioprosthetic heart valve replacements, which utilize biologically derived tissues for flexible fluid occluding leaflets. Another less drastic method for treating defective valves is through repair or reconstruction, which is typically used on minimally calcified valves. One repair technique that has been shown to be effective in treating incompetence is annuloplasty, in which the deformed valve annulus is reshaped by attaching a prosthetic annuloplasty repair segment or ring to the valve annulus.

In a typical cardiac implant procedure, the aorta is incised and, in a valve replacement operation, the defective valve is removed leaving the desired placement site that may include a fibrous tissue layer or annular tissue. Known cardiac implant techniques include individually pre-installing sutures through the fibrous tissue or desired placement site within the valve annulus to form an array of sutures. Free ends of the sutures are draped out of the thoracic cavity and are spaced apart, sometimes being distributed around a suture organizer. The free ends of the sutures are then individually threaded through a suture-permeable sewing edge of the annuloplasty ring or prosthetic heart valve. Once all sutures have been run through the sewing edge (typically 12 to 18 sutures), all the sutures are pulled up taught and the prosthesis is slid or "parachuted" down until it sits against the target annulus. The cardiac implant is then secured in place by traditional knot tying of the anchoring sutures on the proximal side of the sewing edge. There are often 7-10 knots on each suture advanced by pushing the knot one at a time to the desired location by using a knot pusher device. This procedure is obviously time-consuming.

During open-heart procedures, the patient is on heart-lung bypass which reduces the patient's oxygen level and creates non-physiologic blood flow dynamics. The longer a patient is on heart-lung bypass, the greater the risk for complications including permanent health damage. Existing techniques for suturing cardiac implants extend the duration of bypass and increase the health risks due to heart-lung bypass. Furthermore, the securing force created by suturing varies significantly because the pre-tensioning of the suture just prior to knot tying is difficult to consistently maintain, even for an experienced medical professional.

There exists a need for devices and methods that reduce the time required to secure a medical implant in place. Additionally, there exists a need to make it easier to secure a cardiac implant, in particular, in place. Currently, a clinician must work in the limited space near the heart to tie knots in sutures. This is a cumbersome process even for a clinician of great dexterity and patience.

SUMMARY

The present application discloses an installation system for securing an annuloplasty ring or a prosthetic heart valve to a heart valve annulus using knotless suture fasteners. The knotless suture fasteners are desirably spring-biased so as to self-actuate and grip onto annulus anchoring sutures passed therethrough. The system includes a fastener deployment tool with a proximal handle and a distal shaft to which a fastener cartridge attaches. A plurality of disposable cartridges are sequentially attached to the end of the deployment tool and used to secure the medical implant one fastener at a time. The deployment tool may also cut the sutures being fastened.

A preferred embodiment of the present application includes a system for securing a suture without knots, comprising a reusable deployment tool having a distal shaft terminating in a distal tip, the tool including an ejector movable within the distal shaft, and a plurality of pre-assembled, disposable fastener cartridge and suture snare subassemblies. Each subassembly has a cartridge having a lumen that receives a single suture fastener within a distal end thereof, a proximal end of the cartridge lumen being sized to engage the distal tip of the deployment tool shaft. The suture fastener includes clamping structure that can be flexed to an open condition through which a suture can pass and is biased toward a closed position which clamps onto a suture passed therethrough. The cartridge has at least one stop that maintains the suture fastener in its open condition. The subassembly further includes a suture snare having an elongated flexible snare portion size to pass radially inward through aligned ports in the engaged cartridge and tool shaft and distally through the suture fastener in its open condition. The snare portion is adapted to capture and pull a suture proximally through the suture fastener and out of the aligned ports in the cartridge and tool shaft. When the cartridge is engaged with the deployment tool, movement of the ejector contacts and converts the suture fastener from its open condition to its closed condition to clamp onto a suture passed therethrough.

Another system for securing a suture without knots disclosed herein includes a deployment tool with a distal shaft terminating in a distal tip having locking structure thereon, the tool including an ejector movable within the tool shaft, and the tool shaft having a side port adjacent the distal tip. The system includes a suture fastener having clamping structure that can be flexed to an open condition through which a suture can pass and which is biased toward a closed position which clamps onto a suture passed therethrough. A fastener cartridge as a lumen that receives the suture fastener at a distal end and has at least one stop that maintains the suture fastener in its open condition. A proximal end of the cartridge having mating structure for engaging the locking structure of the distal tip of the deployment tool shaft, and the cartridge also has an access port that aligns with the side port of the tool shaft when the two are engaged. Finally, a suture snare includes an elongated flexible snare portion size to pass through the access port of the cartridge, through the side port of the tool shaft, and distally through the suture fastener in its open condition. Movement of the ejector contacts and converts the suture fastener from its open condition to its closed condition to clamp onto a suture passed therethrough.

In either of the systems described above, the deployment tool preferably has a proximal handle with a trigger, and the ejector is longitudinally movable within the tool shaft upon actuation of the trigger. The ejector may further include a sharp edge such that movement thereof also severs a suture extending through the suture fastener and out of the aligned ports in the cartridge and tool shaft.

Preferably, the suture fastener comprises a disk-shaped main body, and the clamping structure comprises at least one tab separated from the main body with slits and being spring-biased toward the closed condition where the tab is aligned with the main body, and the cartridge includes at least one stop that maintains the suture fastener in its open condition flexes the tab away from alignment with the main body.

Desirably, the suture snare comprises a proximal handle connected to the elongated flexible snare portion in the form of a flexible loop, and a grip/key having a peripheral groove for receiving and holding open the flexible loop, and wherein the grip/key is demountably attached to a distal end of the cartridge.

In a preferred embodiment, the cartridge is generally tubular and the proximal end includes an L-shaped slot terminating in a circular lockout that receives a locking pin extending outward from the deployment tool shaft, the cartridge engaging the distal tip of the deployment tool shaft by axially advancing and then rotating thereover to position the locking pin in the circular lockout. The distal tip of the deployment tool shaft may have an L-shaped slot with an axially-extending portion and a circumferential portion, and wherein the axially-extending portion aligns with a first of the aligned ports located on the cartridge to avoid binding on the snare portion when engaging the cartridge to the tool shaft, and the circumferential portion terminates in a second of the aligned ports located on the tool shaft, the first and second aligned ports only being aligned when the cartridge and tool shaft are fully engaged.

In accordance with one aspect, a method for securing an implant without knots initially includes the step of pre-installing a plurality of sutures at an anatomical location and passing the sutures through a suture-permeable portion of an implant. A fastener cartridge and suture snare subassembly is attached to a distal tip of a shaft of a deployment tool. The cartridge has a lumen that receives a single suture fastener within a distal end thereof and at least one stop that maintains clamping structure of the suture fastener in an open condition spring-biased toward a closed condition. The suture snare includes an elongated flexible snare portion sized to pass radially inward through aligned ports in the attached cartridge and tool shaft and distally through the suture fastener in its open condition. The method includes snaring one of the pre-installed sutures with the snare portion, advancing the cartridge along the suture to the implant with the deployment tool until the suture fastener is adjacent to the suture-permeable portion, actuating an ejector within the tool shaft to contact and convert the suture fastener from its open condition to its closed condition in which the clamping structure clamps onto the suture, and severing the suture.

The aforementioned methods may further include one or more of the steps of:
- removing the cartridge from the distal tip of the deployment tool shaft;
- attaching a second fastener cartridge and suture snare subassembly to the distal tip of the deployment tool shaft;
- snaring a second one of the pre-installed sutures with the snare portion;
- advancing the second cartridge along the second suture to the implant with the deployment tool until the second suture fastener is adjacent to the suture-permeable portion;
- actuating an ejector within the tool shaft to contact and convert the second suture fastener from its open condition to its closed condition in which the clamping structure clamps onto the suture; and
- severing the second suture.

The implant is desirably selected from the group consisting of an annuloplasty ring and a heart valve. The suture fasteners preferably each comprise a disk-shaped main body, and the clamping structure comprises at least one tab separated from the main body with slits and being spring-biased toward the closed condition where the tab is aligned with the main body, and the at least one stop that maintains the suture fastener in its open condition flexes the tab away from alignment with the main body. Furthermore, the deployment tool may have a proximal handle with a trigger for actuating the ejector, and the ejector further includes a sharp edge such that movement thereof also severs the suture extending through the suture fastener and out of the aligned ports in the cartridge and tool shaft.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The disclosed technology will now be explained and other advantages and features will appear with reference to the accompanying schematic drawings wherein:

FIG. 3A is a perspective view of an exemplary suture fastener having two tabs that are separated from a generally disc-shaped body by a modified H-shaped slit;

FIG. 3B is another perspective view of the suture fastener of FIG. 3A, showing the fastener engaged with two sutures;

FIG. 3C is a perspective view of another suture fastener again having two tabs and a suture retention recess on each;

FIG. 3D is a perspective view of another suture fastener with two tabs and serpentine sections on both sides of a central slit to help retain sutures therein;

FIG. 4A is a perspective view of another exemplary suture fastener having four tabs that are formed in a generally disc-shaped body;

FIG. 4B is a sectional perspective view of the suture fastener of FIG. 4A engaged with a suture;

FIG. 4C is a plan view and FIG. 4D a side view of the suture fastener of FIG. 4A engaged with a suture;

FIG. 9 is a perspective view of an exemplary system for installing the suture fasteners disclosed in the present application, including a reusable deployment tool and a disposable fastener cartridge and snare subassembly;

FIG. 9A is an enlarged perspective view of the disposable fastener cartridge and snare subassembly adjacent the distal end of the deployment tool;

FIG. 10 is a perspective view of an alternative disposable fastener cartridge and snare subassembly;

FIG. 11A is a longitudinal sectional view of the deployment tool of FIG. 9;

FIGS. 11B-11E are sectional and perspective views of portions of the deployment tool illustrating various moving parts therein;

FIG. 12D is an isolated perspective view of an exemplary internal rib used within the fastener cartridge of FIG. 12A;

FIG. 13A is a top plan view of the disposable fastener cartridge just prior to engagement with a distal tip of the deployment tool, and FIG. 13B is a perspective view of the fastener cartridge after engaging the deployment tool, and showing placement of a suture snare therethrough;

FIGS. 18A-18C show the steps necessary for disengagement of a used fastener cartridge from the distal tip of the deployment tool;

FIG. 19 is a perspective cutaway view of the exemplary disposable fastener cartridge of FIGS. 16A-16D; and FIG. 20 is an exploded perspective view of the fastener cartridge and a suture fastener that is held therein.

DETAILED DESCRIPTION

Figure 1:
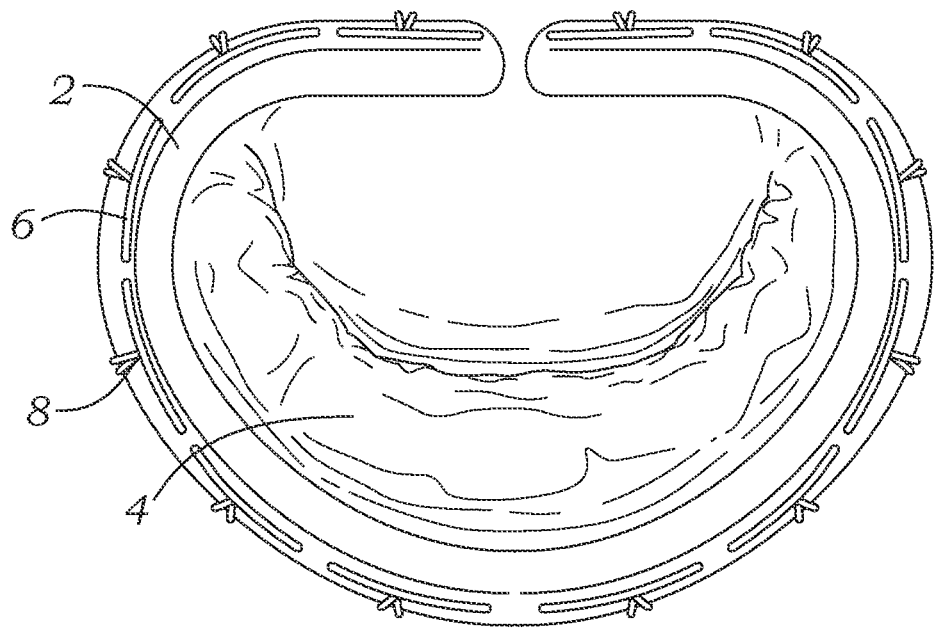
FIG. 1 is a top view of an exemplary annuloplasty ring implanted at the mitral annulus using knotted sutures.

The present application provides improved systems for securing a cardiac implant to a heart valve annulus using knotless suture fasteners. Proximal and distal refer to the opposite directions toward and away, respectively, a surgeon performing the implant. The term cardiac implant as used herein primarily refers to prosthetic heart valves and annuloplasty rings or segments. However, the suture fastening systems described herein can be used to attach other prostheses such as stents, grafts, stent-grafts, fluid delivery reservoirs, electro-stimulators, or the like. Furthermore, the cardiac implants are desirably secured at a target heart valve annulus, but the suture fastening systems may also be used to attach implants to other anatomical structures such as vessels, organs (e.g., intestine, heart, skin, liver, kidney, stomach) or other locations where sutures are typically used to attach the implant. Indeed, the present suture fastening systems can be used to secure tissue structures together, such as for closure of vascular punctures or other wound closure.

Several exemplary embodiments of knotless suture fasteners are disclosed herein and shown in the attached figures. These embodiments should not be construed as limiting in any way. Instead, the present disclosure is directed toward all novel and nonobvious features and aspects of the suture fastening systems described herein, alone and in various combinations and sub-combinations with one another, and regardless of what type of suture fastener is used. The suture fasteners can secure a single suture or to two or more sutures at the same time.

The disclosed suture fasteners all engage a suture by first threading a free end of the suture through an opening in the fastener. For example, the embodiment shown in FIGS. 3 and 4 require that an end of a suture be threaded through an enclosed opening in the suture fastener. One or more biased tabs are held open and then permitted to flex close to clamp onto the suture. The tabs are separated from a main body of the fastener by slits, and the main body is generally disc-shaped, planar or non-planar. The various tabs and other such spring-biased structure are inclusively termed, "clamping structure." Although a biased (spring-biased) type of suture fastener is preferred, certain aspects described herein may be useful with closures that are plastically deformable. For example, the fasteners disclosed in U.S. Pat. No. 5,520,702 to Sauer include a tubular body that is crimped so as to deform around and clamp onto a suture, and such deformable fastener may be used in the systems described herein with certain modifications such as providing a deforming hammer.

Once a knotless suture fastener is positioned on a suture and released, the fastener can prevent the suture from sliding axially through the device in one or both longitudinal directions of the suture. In some embodiments, the device can be biased to allow the suture to slide through the device in one longitudinal direction, but prevent the suture from sliding in the opposite direction, forming a one-way suture lock, or ratchet mechanism. In other embodiments, the device can prevent the suture from sliding in both longitudinal directions, forming a more restrictive two-way suture lock.

By using the disclosed knotless suture fasteners rather than tying knots in the sutures, the sutures can be secured in less time and with less difficulty (especially in hard-to-reach locations). In addition, some knotless suture fasteners can allow the amount of slack left in the sutures to be more precisely controlled, the devices can be less likely to come loose than knots, and some embodiments of the devices can be easily removed or adjusted after they are initially deployed. Furthermore, the knotless suture fasteners can be small, durable, biocompatible, and inexpensive.

Figure 2:
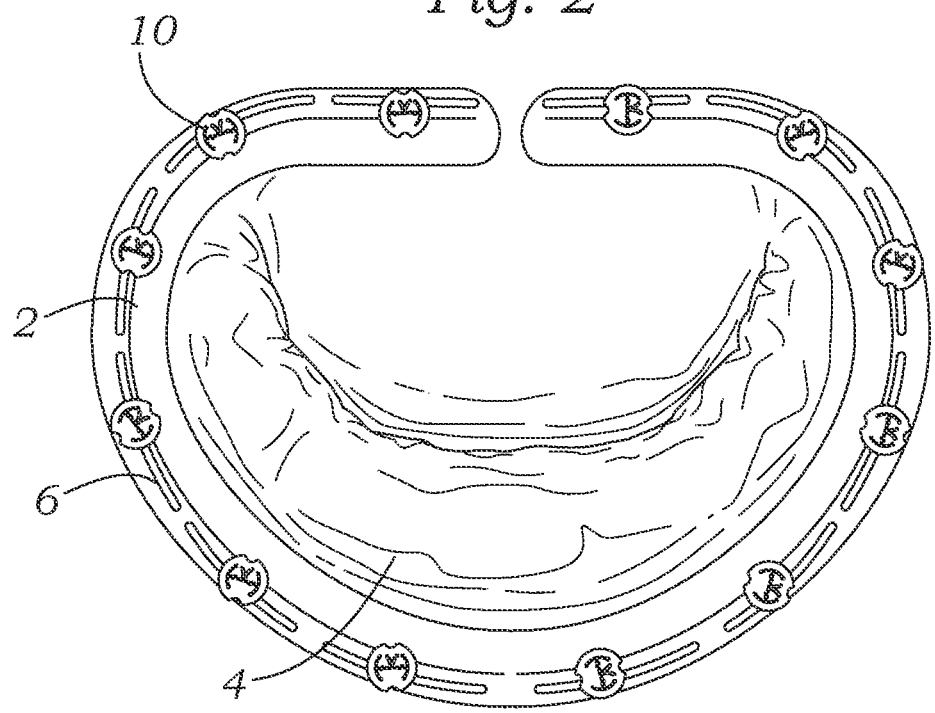
FIG. 2 is a top view of an exemplary annuloplasty ring implanted at the mitral annulus using exemplary suture fasteners in place of knots to secure the sutures.

FIG. 1 shows an exemplary prosthetic device in the form of an annuloplasty ring 2 secured to the annulus of a native mitral valve 4 using sutures 6. Ends of the sutures 6 are secured together using conventional knots 8. FIG. 2 shows the same annuloplasty ring 2 secured to the mitral annulus using exemplary knotless suture fasteners 10 instead of knots. Twelve devices 10 are used in this example, though different numbers of devices can be used in other implementations. In this example, each device 10 secures together two sutures 6 extending generally in parallel and through the annuloplasty ring 2, in place of a standard knot. In other examples, a separate device 10 can be secured to each suture 6 at the location where the suture passes through the annuloplasty ring 2. Either way, the devices 10 prevent the sutures 6 from sliding through the devices toward the annuloplasty ring 2, keeping the sutures taut and keeping the ring 2 secured against the mitral valve tissue 4. In some embodiments, such as the devices 10 shown in FIG. 2, the devices also allow the sutures 6 to be further tightened after an initial deployment to reduce any excess slack in the sutures. Though the exemplary knotless suture fasteners 10 are shown in the example of FIG. 2, any of the embodiments disclosed herein can be used for the same or similar purposes on other implementations.

While FIG. 2 shows an annuloplasty ring being secured by devices 10, the devices 10, as well as the other embodiments of knotless suture fasteners disclosed herein, can be used to secure other prosthetic devices to tissue in the body. Other prosthetic devices include, for example, prosthetic heart valves, stents, grafts, and various other prosthetic implants conventionally secured to tissue using sutures.

FIGS. 3A and 3B show embodiments of a closed, non-biased suture fastener 30. The suture fastener 30 comprises a generally flat disk-shaped body having an annular outer edge 32 and two tabs 34, 36 as clamping structure that extend inwardly from the outer edge 32. Each tab 34, 36 is shaped generally in a half-circle. The tabs 34, 36 are separated from the outer body at their sides by curved slots 38, 40 and are separated from each other by a straight slit 42 generally bifurcating the suture fastener 30. The curved slots 38, 40 and middle slit 42 connect to each other but do not intersect with an outer edge 32, thus forming a "closed" generally H-shaped opening extending from one face of the suture fastener to the other. In the closed condition, the tabs 34, 36 are aligned with the disk-shaped body. One or more sutures 43 can be inserted into the slit 42 from either the top or the bottom, deflecting both tabs 34, 36 in the direction of insertion, as shown in FIG. 3B. Once the sutures 43 are inserted as shown in FIG. 3B, the suture fastener 30 is biased toward its relaxed, flat configuration, and allows the sutures to move axially upward with little resistance but prevents the sutures from moving axially downward. In some embodiments, the gripping edges of the tabs 34, 36 can be sharp (see FIG. 3A), which can provide better grip on the sutures, and in other embodiments the gripping edges of the tabs can be rounded (see FIG. 3B), which can reduce the likelihood of damaging and/or cutting the sutures. In some implementations of the suture fastener 30 (not shown), the two tabs 34, 36 can be elastically deformed in opposite directions with one tab bending upwardly out-of-plane and the other tab bending downwardly out-of-plane. This can lock the sutures from sliding in either direction through the suture fastener 30. The two sutures 43 shown in FIG. 3B can correspond to free ends of the sutures 6 shown in FIG. 2, for example.

FIG. 3C shows a suture fastener 44 that is a variation of the suture fastener 30 wherein the gripping surfaces of the tabs 34, 36 comprise notched or recess regions 45 that can help contain the sutures within the slit 42 and prevent them from sliding into the curved slits 38, 40.

FIG. 3D shows a still further variation of the suture fastener 46 having a flat generally disk-shaped body having an annular outer edge 32' and two tabs 34', 36' as clamping structure that extend inwardly therefrom. As in FIG. 3A, each tab 34', 36' is shaped generally in a half-circle. The tabs 34', 36' are separated from the outer body at their sides by curved slots 38', 40' and are separated from each other by a slit 42' that has a straight midsection. Once again, the curved slots 38', 40' and middle slit 42' connect to each other but do not intersect with an outer edge of the body 32', thus forming a "closed" generally H-shaped opening extending from one face of the suture fastener to the other. In a closed condition, the tabs 34', 36' are aligned with the disk-shaped body. One or more sutures can be inserted into the slit 42 from either the top or the bottom, deflecting both tabs 34, 36 in the direction of insertion, as was shown in FIG. 3B. Once the sutures 43 are inserted in the slit 42, the suture fastener 46 becomes biased and allows the sutures to move axially upward with little resistance but prevents the sutures from moving axially downward. As mentioned above, the gripping edges of the tabs 34, 36 may be sharp for better grip on the sutures, or rounded to reduce the likelihood of damaging and/or cutting the sutures.

To help retain sutures in the midsection of the slit 42', the slit includes serpentine sections 47 on either side. The tabs 34', 36' are identical, or mirror images of each other, though one may be larger than the other. Small circular enlargements 48 on the terminal end of each curved slot 38', 40' facilitate bending of the tabs 34', 36' and act as stress relievers to reduce the chance of fracture at those points. Two semi-circular cutouts 49 are provided on opposite sides of the outer edge 32' perpendicular to the straight section of the slit 42'. The cutouts 48 provide orientation features for the suture fastener 46 that cooperate with features on a tool (not shown) which can hold and deploy multiple suture fasteners in series.

FIGS. 4A-4D show an embodiment of a closed, biased suture fastener 50. The suture fastener 50 comprises an annular outer body 52, and two engagement tabs 54, 56 and two side tabs 58, 60 extending inwardly from the outer body 52. The tabs 54, 56 and/or the tabs 58, 60 can also extend upwardly out-of-plane from the outer body 52. The engagement tabs 54, 56 can comprise concave engagement surfaces 62 to keep the suture 64 centered between them. The side tabs 58, 60 can prevent the suture 64 from sliding laterally out from between the engagement tabs 54, 56. The engagement tabs 54, 56 are biased to allow the suture 64 to slide upwardly through the suture fastener 50 with little resistance but prevent the suture from sliding downwardly through the suture fastener.

Some suture fasteners can be relatively thin, disk-shaped members but have a generally curved rather than a planar shape. The embodiments shown in FIGS. 5-8 are examples of suture fasteners having a curved shape. In these embodiments, the suture fastener can have an upper major surface that is generally convex and a lower major surface that is generally concave. The upper and lower major surfaces are substantially parallel to each other, with the suture fasteners having a substantially constant thickness between the two major surfaces. In some embodiments, the upper and lower major surfaces are curved in one direction and non-curved in a perpendicular direction (like a sidewall of a cylinder), such that the surfaces have central axis of curvature. In some embodiments, both major surfaces have a common central axis of curvature. In other embodiments, the major surfaces are curved in other manners, such as having concentric spherical major surfaces that share a common center of curvature. By providing suture fasteners with a curved structure, the fasteners can be biased to provide greater resistance to sutures moving toward the concave direction while more readily allowing sutures to move toward the convex direction.

In some embodiments, such curved suture fasteners are formed from a sidewall of a tube. The outer radius of the tube can define the curvature of the convex major surface of the suture fastener while the inner radius of the tube can define the curvature of the concave major surface of the device. The uniform thickness of a curved suture fastener is equal to the wall thickness of the tube that the device is cut from. In other embodiments, the suture fasteners are formed from a sidewall of a non-cylindrical tube, or from a wall of other three-dimensional objects having a curved wall, such as a hollow sphere, spheroid, ellipsoid, etc., or from other three-dimensional objects having a curvature.

Figure 5:
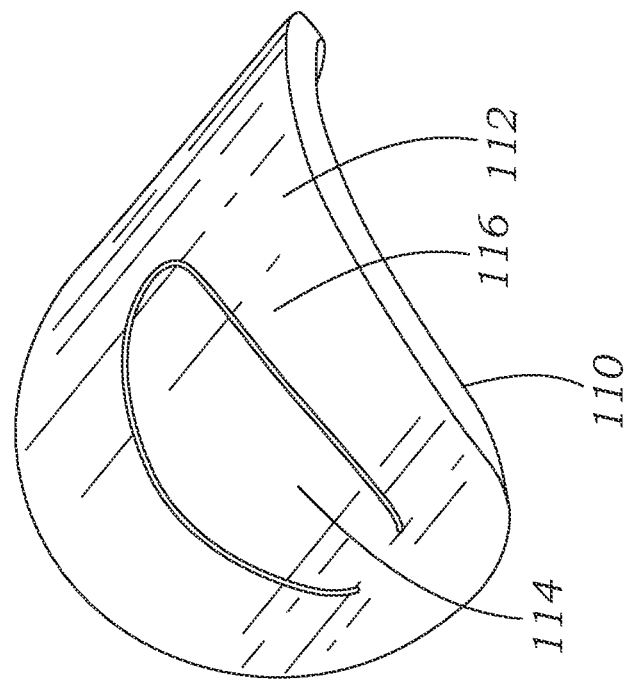

FIG. 5 shows an exemplary embodiment of a curved suture fastener boo. The suture fastener 100 comprises an annular outer body 102 and an inner body, or tab, 104 that is separated from the outer body by a "C" shaped slit 106. The convex, upper major surface of the suture fastener 100 is shown in FIG. 5. The tab 104 has an elliptical shape and extends from a connection to the outer body in the direction of the curvature of the suture fastener. One or more sutures can be inserted through the slit 106 from the concave, lower side of the suture fastener 100, causing the tab 104 to deflect upwardly. With sutures inserted through the slit 106, the biased tab 104 pinches the sutures and prevents them from sliding back through the slit toward the concave direction. Thus, the suture fastener 100 is attached to sutures with the concave side of the fastener facing a prosthetic device or tissue from which the free ends of the sutures extend.

Figure 6:
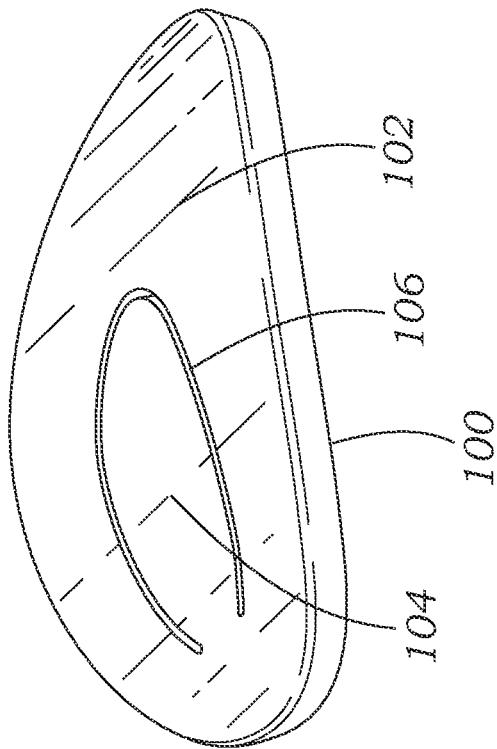
FIGS. 5 and 6 are perspective views of exemplary curved suture fasteners having C-shaped slits forming a biased tab.

FIG. 6 shows an alternative embodiment of a curved suture fastener 110 that is similar to the fastener 100 but has greater curvature. The suture fastener 110 comprises an annular outer body 112, an inner tab 114, and a "C" shaped slit 116. The increased curvature of the suture fastener 110 relative to the fastener 100 results in increased bias and increased resistance to sutures sliding through the slit 116 toward the concave direction. The embodiments 100 and 110 represent two examples of different curvatures, while other embodiments can have any other degree of curvature desired. Similarly, the thickness of the curved suture fasteners may vary and is typically selected to provide a desired stiffness for the fastener.

Figure 7:
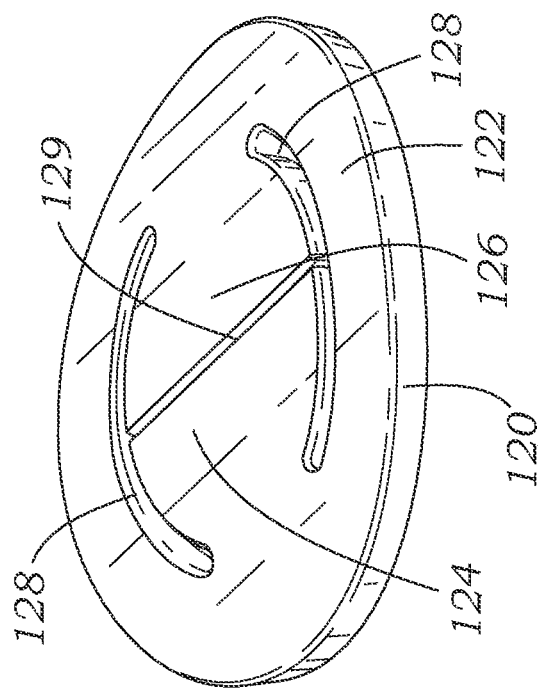

FIG. 7 shows an embodiment of a curved suture securement suture fastener 120 that comprises an annular outer body 122 and two opposing tabs 124, 126, similar to a flat version shown in FIGS. 3A-3C. The outer body 122 has a generally circular shape and each of the tabs 124, 126 has a generally half-circle shape. The tabs 124, 126 are separated from the outer body by two arcuate slots 128 and the tabs are separated from each other by a straight slit 129 that connects the two arcuate slots 128. One or more sutures can be inserted into the slit 129 from the lower convex side, deflecting both tabs 124, 126 upwardly in the direction of insertion. With the sutures inserted, the biased tabs allow the sutures to move upwardly in the convex direction with little resistance but prevent the sutures from moving downwardly in the concave direction.

Figure 8:
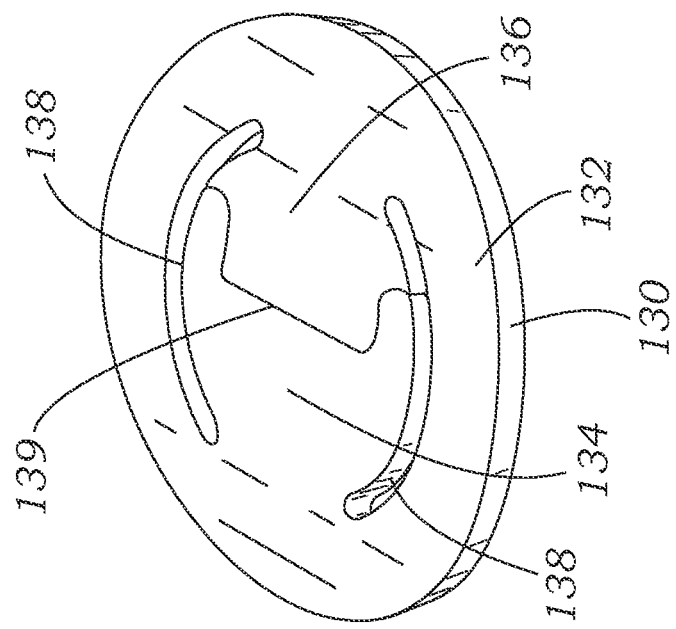
FIGS. 7 and 8 are perspective views of two other suture fasteners having two tabs that are separated from a curved body.

FIG. 8 shows another embodiment of a curved suture securement suture fastener 130 that comprises an annular outer body 132 and two opposing tabs 134, 136. The outer body 132 has a generally circular shape and each of the tabs 134, 126 extends inwardly from opposite ends of the outer body. The tabs 134, 136 are separated from the outer body by two arcuate slots 138 and the tabs are separated from each other by a slit 139 that connects the two arcuate slots 138. The slit 139 preferably has a straight middle portion for placement of sutures and angled or L-shaped end portions 131 at either end of the straight portion that help retain the sutures in the straight portion of the slit 139 and prevent the sutures from migrating into the arcuate slots 138. The two tabs 134, 136 are thus dissimilar, with the larger left tab 134 extending around the right tab 136 on both sides at the L-shaped end portions 131 of the slit 139. One or more sutures can be inserted into the slit 139 from the lower convex side, deflecting both tabs 134, 136 upwardly in the direction of insertion. With the sutures inserted, the biased tabs allow the sutures to move upwardly in the convex direction with little resistance but prevent the sutures from moving downwardly in the concave direction.

The suture fasteners disclosed herein may be formed from suitable biocompatible material, including, for example, Nickel-Titanium or other shape-memory alloys, stainless steel, titanium, other metals, various plastics, and other biologically-compatible materials. The illustrated suture fasteners are mostly flat or curved disc-shaped bodies which are relatively thin axially, and may be up to about 1-2 mm in height. The diameter of the suture fasteners may be between 2-4 mm, but only needs to be sufficiently large to be incapable of penetrating a suture-permeable sewing edge of a cardiac implant, such as a sewing ring of a prosthetic heart valve or an annuloplasty ring. That is, the suture fasteners are wide enough to avoid being pulled through a sewing edge of a cardiac implant when the sutures captured therein are placed under tension.

Braided sutures are used to attach prosthetic heart valves to annuluses as opposed to monofilament polypropylene sutures (e.g., Prolene) which are used in other surgical environments. In the United States, suture diameter is represented on a scale descending from 10 to 1, and then descending again from 1-0 to 12-0. A number 9 suture is 0.0012 in (0.03 mm) in diameter, while the smallest, number 12-0, is smaller in diameter than a human hair. Although suture size depends on surgeon preference, typically 1-0 or 2-0 braided sutures are used. In one embodiment, if larger sutures are used the diameter of the suture fastener is up to 4 mm, while if smaller sutures, such as 2-0, are used the diameter may be as small as 2 mm.

The knotless suture fasteners described herein include self-actuating or spring-loaded devices that clamp onto sutures. Passing one or more sutures through the suture fastener and then converting it from an open to a closed state causes features to collapse inward and clamp onto the suture(s). The conversion desirably occurs upon removal of an impediment to inward motion of clamping elements, though other spring-loaded configurations are possible. Such self-actuating suture fasteners are preferred over plastically-deformable fasteners which must be crimped over the sutures using forceps or other such compression tools. On the other hand, for added security a supplemental portion (not shown) of the suture fasteners disclosed herein may be deformable so that a user may crimp it onto the sutures—a hybrid fastener. For the purpose of defining terms, the term "self-actuating" suture fastener refers to a spring-biased type of device which does not require crimping, but which, on the other hand, does not exclude a crimpable portion. A "self-actuating" suture fastener is not entirely autonomous, in that there is a trigger prior to the deployment, such as removal of an element or change in temperature, but the term excludes devices that require mechanical crimping using a supplemental tool such as a hammer and anvil system.

Alternative self-actuating fasteners may be made of a temperature-activated memory material that biases the fastener to its closed configuration when exposed to a selected temperature range, though the control and timing of such devices add complexity. With the temperature-activated memory material in its austenite state, the fastener tabs extend into the inner lumen to their greatest extent, so that the fastener is in a "closed" configuration wherein the tabs block movement of any lengths of suture passing through the inner lumen. The austenite state can be set to occur when the suture fastener is generally unstressed and at human body temperature, so that when deployed in the patient's body it will be remain biased toward its closed configuration.

Fastener Deployment Tools

FIG. 9 shows an exemplary fastener deployment tool 200 for installing the suture fasteners disclosed in the present application having a proximal handle 202 and an elongated distal shaft 204 extending therefrom. The handle incorporates a trigger actuator 206, though other actuators are contemplated. The total length of the deployment tool 200, and at least the length of the shaft 204, should be sufficient to extend from outside the surgical site to the aortic annulus, such as between about 10-16 inches. The deployment tool 200 is intended to be reused during a surgical procedure, and is preferably made of materials that enable sterilization for a subsequent procedure. For instance, the outer shaft 204 is made from stainless steel tube, and may be available in multiple lengths to facilitate a variety of surgical techniques during heart valve repair or replacement, or for implant of other medical devices. An exemplary OD of the shaft 204 is about 3.2 mm (⅛ inch).

A subassembly 210 including a disposable fastener cartridge 212 and suture snare 214 is configured to mate with a distal tip 216 of the deployment tool shaft 204, and as such is shown slightly removed therefrom in FIGS. 9 and 9A. The suture snare 214 may take a number of forms, and as illustrated includes a proximal pull tab 218 connected to a snare portion comprising a distal loop, hook or snare end 220 and a flexible wire or strip 222. In a preferred embodiment, the strip 222 is flexible stainless steel, and may also be configured as a wire or wire loop as seen below. As will be explained below, the snare end 220 and flexible strip 222 are fed through apertures and passages in the disposable fastener cartridge 212 so that the snare end extends from a distal end of and generally along a central axis of the cartridge as shown.

An alternative embodiment of a suture snare 224 shown in FIG. 10 includes a distal wire loop 226 connected to a proximal handle 228 in the form of a bulb. The wire loop 226 is initially routed around a peripheral groove in a placement grip/key 229 for shipping, storage and handling purposes and to prevent kinking of the loop. Either of the suture snares 214, 224 may be used and provide a means for grasping one or more sutures and pulling them through passageways in the fastener cartridge 212. The length of the flexible strip 222 or wire loop 226 beyond the respective handle pull tab 218 or handle 228 is sufficient to pass through the fastener cartridge 212 and extend beyond a sufficient distance to enable grasping of sutures; the length being, for example, between about 2-8 inches.

FIG. 11A is a longitudinal sectional view of the deployment tool 200 of FIG. 9 showing internal components, while FIGS. 11B-11D are detailed views illustrating key moving parts therein. More particularly, the handle 202 typically comprises a pair of molded halves defining a cavity therein in which the trigger actuator 206 reciprocates. Pushing the actuator 206 inward, as indicated in FIG. 11B, rotates a lever arm 230 about a pivot point 232. The upper end of the lever arm 230 acts via a linkage on a push rod 234 adapted to reciprocate within the hollow tool shaft 204. Consequently, the depression of the trigger actuator 206 causes distal displacement of the push rod 234, while a spring return (not shown) of the trigger actuator retracts the push rod proximally.

With reference to FIGS. 11C and 11D, the distal end of the push rod 234 fastens to a proximal end of a fastener ejector 236 having a main body portion which fits closely in the lumen of the tool shaft 204. The ejector 236 also has pair of bifurcated fingers 238 projecting from a distal end. It should be noted that a distal shoulder 240 located at the transition between the main body of the ejector 206 and the distal fingers 238 has a relatively sharp corner angle, the purpose of which will be described below.

As seen in FIGS. 11D and 11E, the distal tip 216 of the tool shaft 204 also features an outwardly projecting locking pin 242 and a side port 244 generally opposite the pin for cooperating with the fastener cartridge and suture snare subassembly 210. The side port 244 opens to the distal tip 216 via an L-shaped slot 246 having a circumferential portion 248a and an axial portion 248b. As will be described below with reference to coupling of the fastener cartridge 212 with the tool shaft 204, the L-shaped slot 246 enables pull through of the suture snare 214 upon registration of the shaft with the cartridge.

Figure 12A:
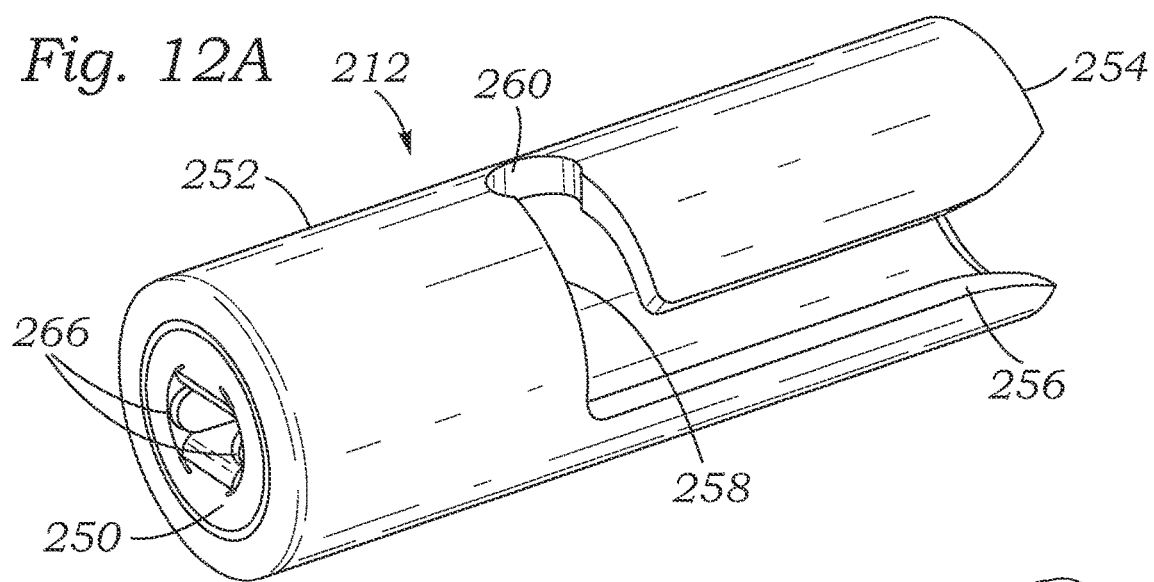
FIG. 12A is a perspective view of the distal end of an exemplary disposable fastener cartridge.

FIG. 12A is a perspective view of an exemplary disposable fastener cartridge 212, showing an exemplary suture fastener 250 held at a distal end thereof. The cartridge 212 has a generally tubular body 252 with an open proximal mouth 254 with an axial slot 256 opening on one side thereof. The slot 256 has a flared open end and intersects with a circumferential slot 258 approximately midway along the length of the cartridge body 252. The slot 258 terminates at a circular lockout 260. The combination of the axial slot 256, circumferential slot 258, and lockout 260 forms a bayonet-style latch that engages the distal tip 216 of the tool shaft 204, as will be shown. It should be noted that the illustrated locking structure provided on the deployment tool shaft 204 that engages the mating structure on the cartridge 212 is exemplary only, and other such configurations are contemplated. For example, the cartridge 212 may include threads that engage similar threads on the tool shaft 204, or the connection may be a spring-loaded bearing on the shaft 204 which snap fits into a groove on the cartridge 212.

Figure 12B:
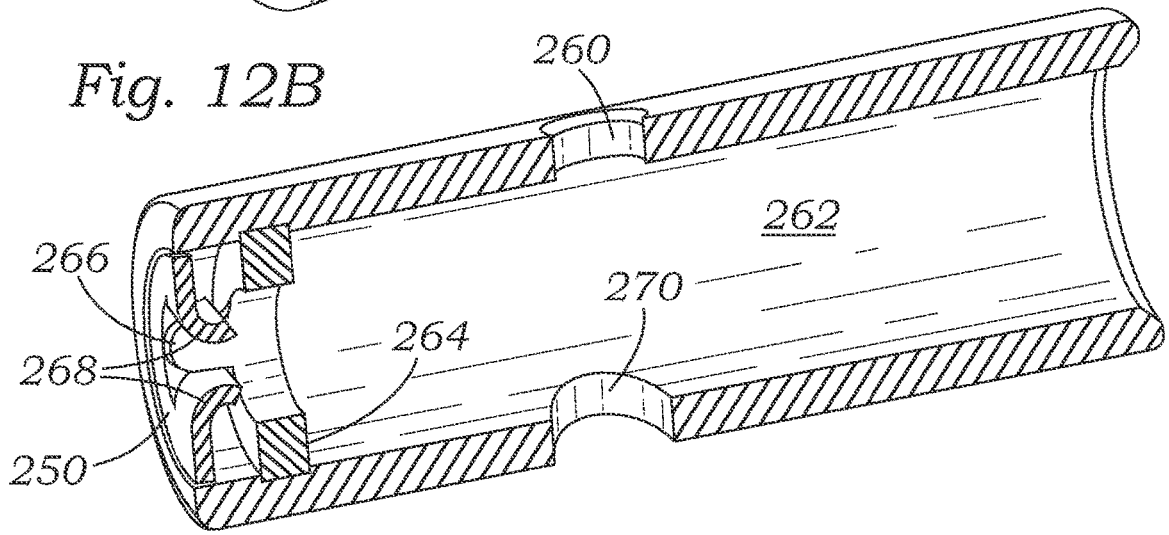
FIGS. 12B and 12C are sectional views of the fastener cartridge of FIG. 12A showing a fastener at the distal end held open by internal features, and illustrating the path of a suture snare therethrough.
Figure 12C:
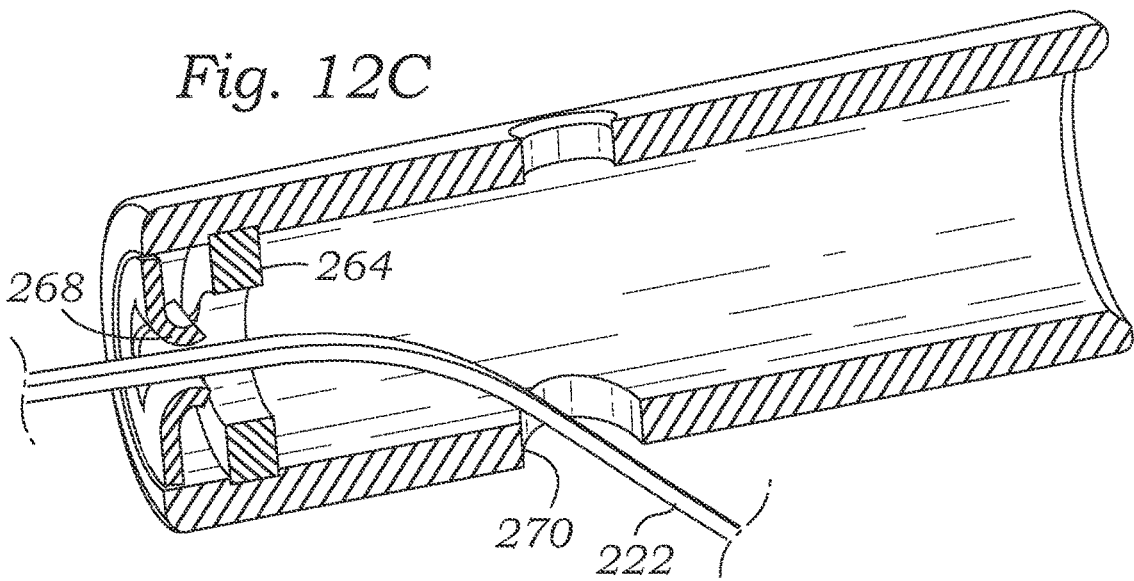

With reference to the sectional views of FIGS. 12B and 12C, the body 252 defines an inner lumen 262 that has a continuous diameter for most of its length except for a generally annular inwardly directed rib 264 near its distal end. The rib 264 extends around the perimeter of the lumen 262 and has a pair of stops 266 projecting in a distal direction on opposite sides and spaced inward from the lumen 262. The stops 266 hold open two biased tabs 268 on the suture fastener 250 for passage of the suture snare and, ultimately, the sutures. The rib 264 having the stops 266 is shown isolated in FIG. 12D, and generally comprises a ring-shaped element with a square cross-section. The disposable fastener cartridge 212 preferably comprises a thermoplastic molded over the rib 264, which is preferably metal such as stainless steel, or more preferably a cobalt-chromium alloy. The stainless steel rib 264 and its stops 266 are sufficiently hard to maintain the suture fastener 250 in an open position without deformation, while the cartridge 212 as a whole is a relatively inexpensive item. In any one procedure, ten or more of the cartridges 212 and fasteners 250 may be used and discarded with minimal expense. The deployment tool 200 is preferably reused, at least for the one procedure, and then may be sterilized for subsequent use.

The fastener 250 may be any of the fasteners described above, such as those shown in FIGS. 3A-3D which have at least one and preferably two biased tabs 34, 36 separated from a generally disc shaped body by slits. Although not shown, those of skill in the art will understand that a separate assembly fixture (not shown) may be required to bias the tabs 268 open and load the fastener 250 into the position held open by the projections 266 as shown in FIGS. 12A-12C. The fasteners 250 are typically formed a highly flexible stainless steel or superelastic such as Nitinol.

The cartridge body 252 also includes an access port 270 typically located opposite the lockout 260. As seen in FIG. 12C, the flexible strip 222 of the suture snare 214 passes into the access port 270, through the distal tip 216 of the tool shaft 204 (not shown), and distally through a central opening in the annular rib 264 and between the open suture fastener tabs 268. A full explanation of the cooperation between the various deployment components will be clear below.

FIG. 13A is a top plan view of the disposable fastener cartridge 212 just prior to engagement with the distal tip 216 of the deployment tool shaft 204. To couple the two components, the cartridge 212 is displaced to the right so that the locking pin 242 on the shaft 204 enters the axial slot 256 on the cartridge. The distal tip 216 fits closely within the lumen 262 of the cartridge 212, and eventually the pin 242 reaches the end of the slot 256. The reader will notice that the axial portion 248b of the L-shaped slot 246 on the shaft 204 is aligned with the access port 270 on the cartridge 212, and thus travels over the segment of the flexible strip 222 of the suture snare 214 that extends diagonally through the distal end of the cartridge.

FIG. 13B shows the fastener cartridge being rotated or twisted in the clockwise direction relative to the shaft 204 so that the pin 242 travels along the circumferential slot 258 until it reaches the lockout 260. In a preferred embodiment, the pin 242 is slightly wider than the slot 258, so that it "snaps" in to place within the lockout 260 as a tactile and audible indicator of full engagement. It will be understood that the circumferential portion 248a of the L-shaped slot 246 on the shaft 204 accommodates the flexible strip 222 as the cartridge and shaft are relatively rotated. That is, the flexible strip 222 as well as the access port 270 on the cartridge 212 eventually end up in registry with the side port 244 on the shaft 204 (see FIGS. 11C and 11E).

Figure 14A:
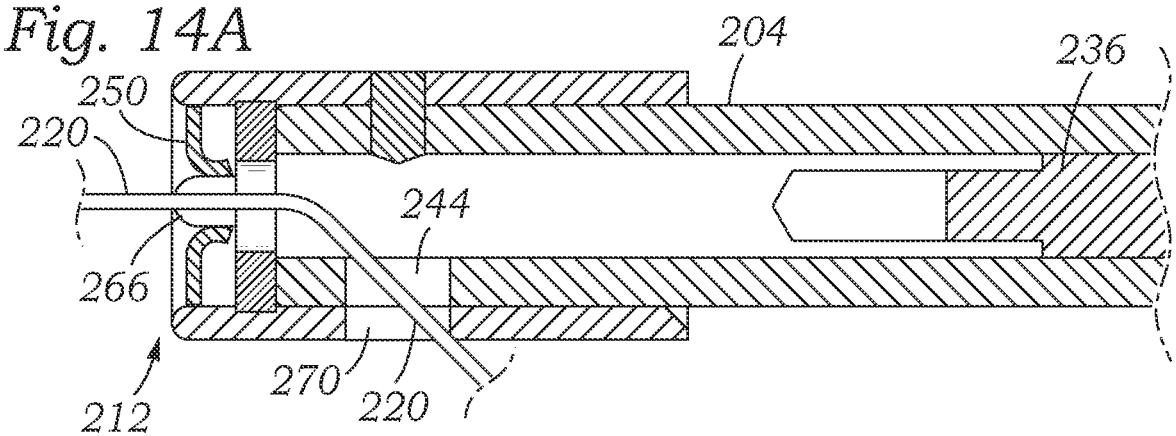
FIGS. 14A-14D are longitudinal sectional views through the disposable fastener cartridge on the end of the deployment tool illustrating steps in deploying the suture fastener.
Figure 14B:
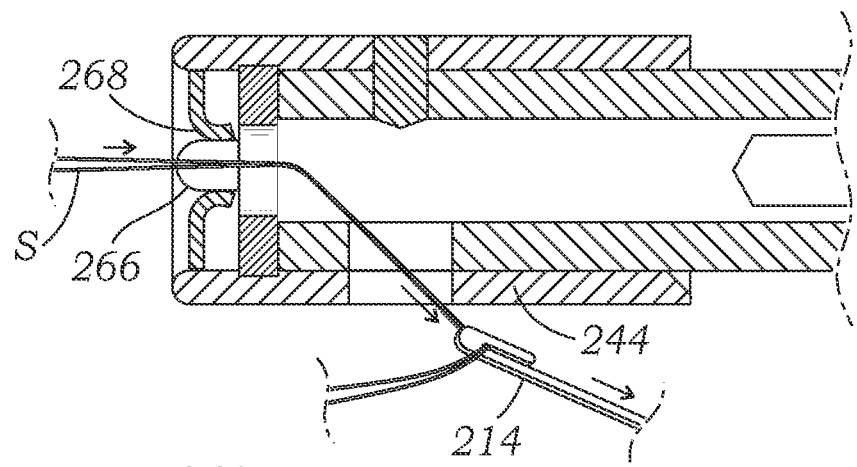

FIGS. 13A and 13B show placement of the flexible strip 222 of the suture snare 214 through the engaged components. More particularly, the strip 222 extends radially inward through the access port 270 in the cartridge body 252, through the port 244 (see FIG. 11C) in the shaft 204, and then axially through the open fastener 250. This is also illustrated in FIG. 14A. Because of the L-shaped slots formed in both the shaft 204 and cartridge 212, the suture snare 214 is ready to use once the two components are joined together. That is, the subassembly of the cartridge 212 and suture snare 214 are pre-assemble and packaged in combination with a number of other subassemblies (i.e., packs of 6) for use with one of the delivery tools 200. By simply coupling each cartridge subassembly to the tool shaft 204, as explained above, the delivery system is ready to install the suture fastener 250.

FIGS. 14A-14D are longitudinal sectional views through the disposable fastener cartridge 212 engaged with the end of the deployment tool 200, and illustrating steps in deploying the suture fastener 250. The assembly described above is first shown in FIG. 14A, which is the configuration just prior to introduction of the tool 200 to the implantation site for deployment of the fastener 250. The deployment sequence can also be understood with reference to FIGS. 15A-15B, which will be described in parallel.

Figure 15A:
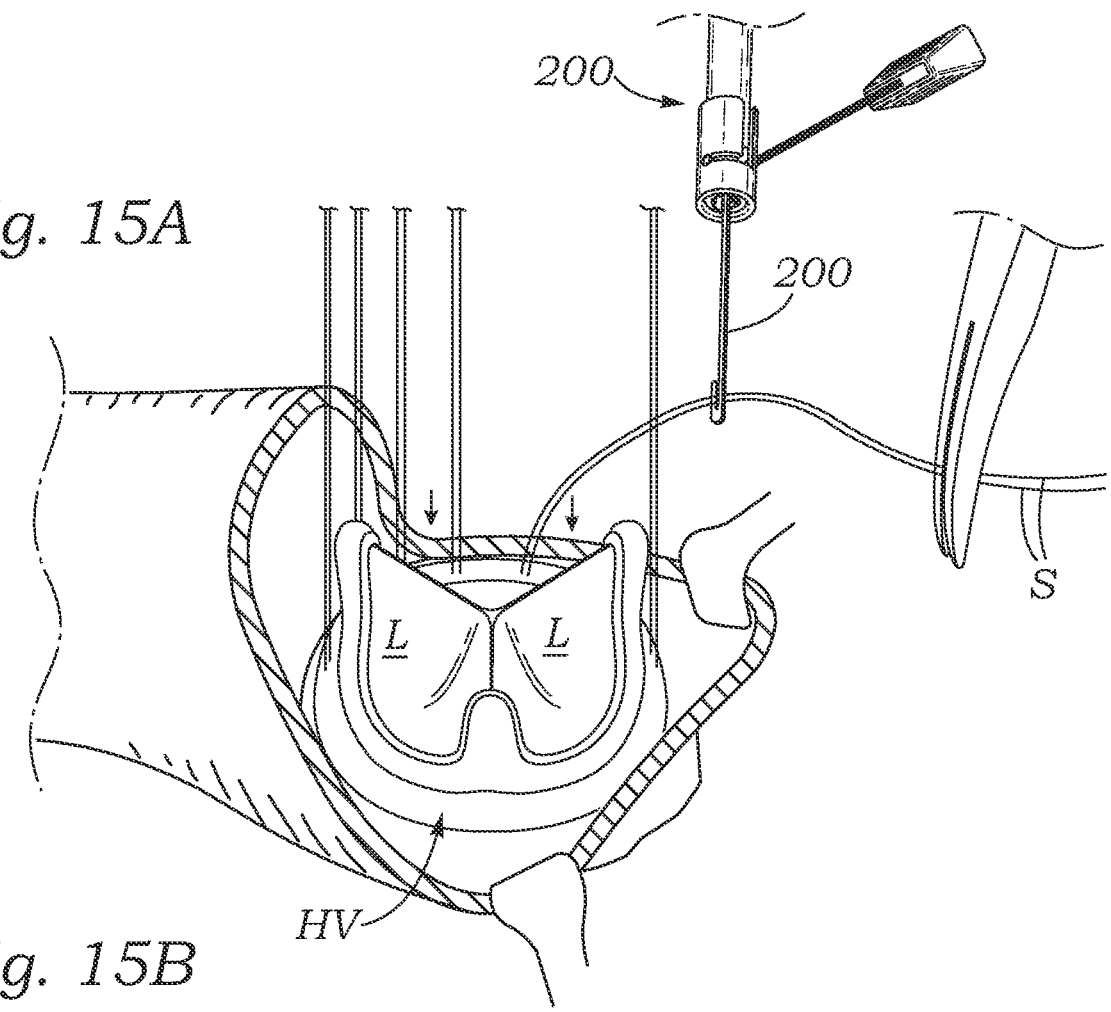
FIG. 15A is a perspective cutaway view of an aortic annulus showing a step in attachment of a surgical prosthetic heart valve using knotless suture fasteners and a deployment tool of the present application.

FIG. 15A illustrates an ascending aorta opened up during a step in attachment of a surgical prosthetic heart valve HV to the aortic annulus using knotless suture fasteners 250. The heart valve HV is of a type having flexible leaflets L supported by commissure posts that extend in an outflow direction of the valve. The commissure posts form a part of an internal support frame (not shown) typically covered by fabric. Secured around an inflow end of the support frame, a peripheral sewing ring SR provides an anchoring zone for a plurality of anchoring sutures S that are pre-installed at the aortic annulus.

The surgeon pre-attaches the anchoring sutures S at evenly spaced locations around the aortic annulus. The anchoring sutures S are typically looped twice through the annulus from the outflow or ascending aorta side to the inflow or ventricular side. Of course, other suturing methods or pledgets may be used depending on surgeon preference. Once each anchoring suture S is secured to the annulus, it extends proximally in pairs of free lengths out of the operating site. The heart valve HV is typically mounted on a valve holder and delivery handle (not shown), and the surgeon threads the pairs of anchoring sutures S through evenly spaced locations around the sewing ring SR corresponding to their locations around the annulus. The surgeon then advances the valve HV into position within the aortic annulus along the array of anchoring sutures S. Some of the anchoring sutures S are not shown around the front of the heart valve HV in FIG. 15A for clarity.

Subsequently, the surgeon installs a suture fastener 250 on each pair of anchoring sutures S on the proximal or outflow side of the sewing ring SR. This is accomplished using the fastener deployment tool 200 in conjunction with the suture snare 214. First, the surgeon captures two free lengths of a pair of anchoring sutures S with the snare end 220 of the snare 214 using forceps, for example. Subsequently, the surgeon pulls the suture snare 214 proximally through and out of engagement with the deployment tool 200, as indicated by the arrows in FIG. 14B. This pulls the anchoring sutures S through the suture fastener 250, through the internal channels of the cartridge 212 and deployment tool 200, and out of the side port 244.

Figure 14C:
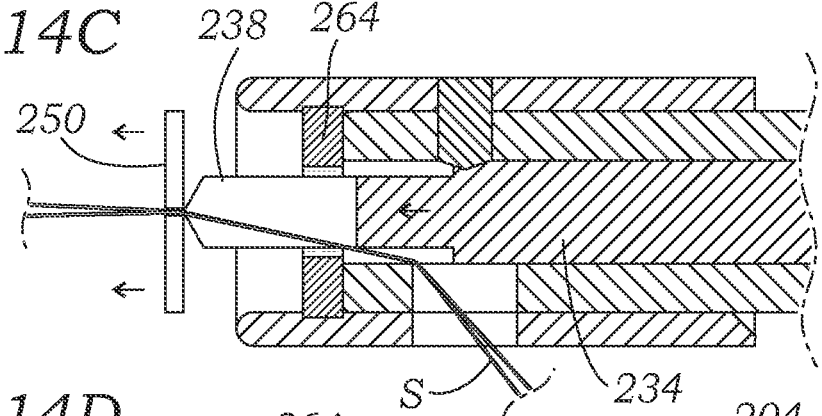
Figure 15B:
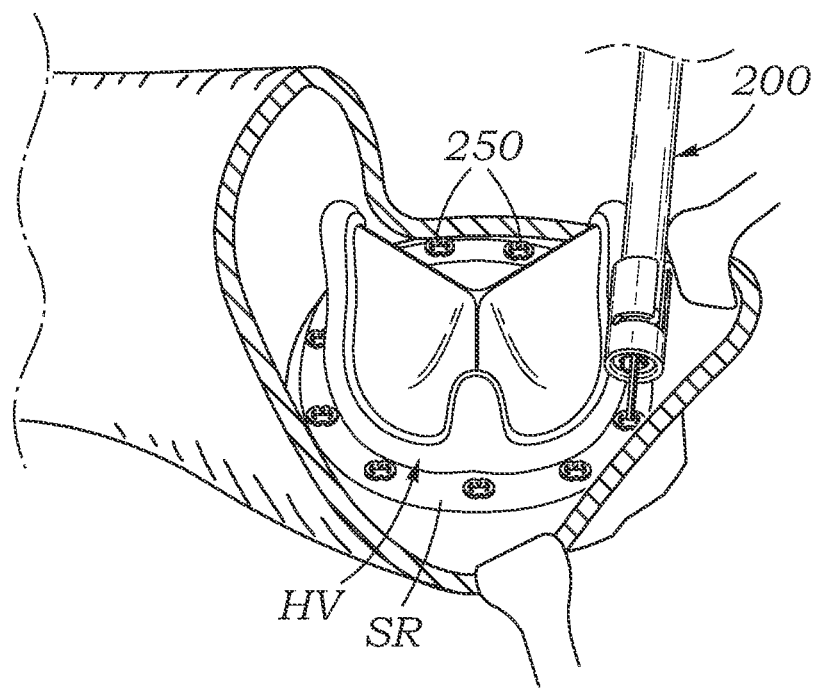
FIG. 15B is a view as in FIG. 15A showing a final step in attachment of the prosthetic heart valve with the knotless suture fasteners and deployment tool.

The surgeon then maintains tension on the anchoring sutures S through the side port 244, and advances the shaft 204 of the deployment tool 200 distally until it contacts the valve sewing ring SR. The suture fastener 250 is then deployed using the trigger actuator 206 (FIG. 9) on the deployment tool 200, as will be explained with reference to FIGS. 14C and 40D, so that it clamps down on the anchoring sutures S. The deployment tool 200 can then be retracted and the anchoring sutures S severed just above the suture fastener 250 using scissors or a cutter integrated with the deployment tool. FIG. 15B shows a majority of the fasteners 250 already installed around the sewing ring SR to secure the heart valve HV to the aortic annulus.

After pulling the sutures S in a proximal direction through the fastener 250, cartridge 212 and deployment tool 200, the surgeon triggers the actuator 206 which displaces the push rod 234 distally. As seen in FIG. 14C, the bifurcated fingers 238 at the distal end of the ejector 236 eventually contact the inwardly bent tabs 268 and force the suture fastener 250 out of the cartridge 212. The fingers 238 have a reduced diameter relative to the body of the ejector 236 so as to fit through the central opening of the annular rib 264. Furthermore, the bifurcated nature of the fingers 238 provides a passageway for the sutures S and prevents the fingers from binding the sutures, such as against the fastener 250. As soon as the fastener 250 is pushed off of the stops 266, the biased tabs 268 spring back toward their natural, relaxed shape (which, in the illustrated embodiment is in the plane of the rest of the fastener), clamping down on the sutures S. Assuming the surgeon has positioned the distal end of the cartridge 212 against the heart valve sewing ring SR, the fastener 250 provides an anchor to hold the sewing ring against the annulus at that point.

Figure 14D:
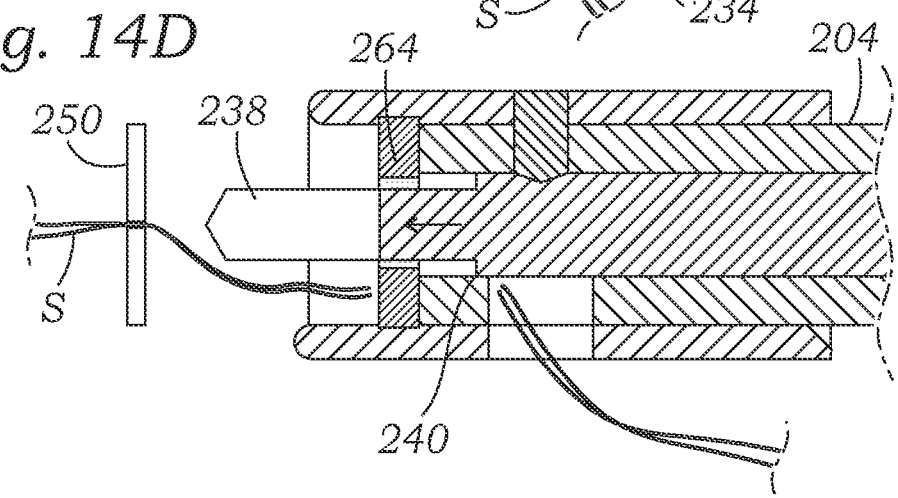

Now with reference to FIG. 14D, further deployment of the actuator 206 and distal displacement of the push rod 234 severs the sutures S. In particular, the sharp corner 240 on the ejector 236 travels past the distal edge of the side port 244 in the deployment tool shaft 204. The side port 244 may also have a sharp corner, and the interaction between these two sharp corners creates a shearing action sufficient to sever the sutures S. Of course, this step may be omitted in favor of simply cutting sutures S close to the fastener 250 after removing the tool 200.

The heart valve HV is representative of numerous types of heart valves, including those with flexible leaflets as shown and also mechanical valves with rigid metallic leaflets, in addition to other surgical implants as mentioned above. Further, the flexible leaflet heart valve HV is shown with the suture fasteners 250 deployed from an outflow side of the valve, which typically indicates that the valve is for implant at the aortic annulus where the outflow is also the proximal side relative to conventional heart valve delivery. However, it should be understood that the suture fasteners 250 could be reversed within the heart valve HV so that they are deployed from the inflow side, such as in a mitral valve replacement procedure.

FIGS. 16A-16D illustrate an exemplary disposable fastener cartridge 212 with an alternative suture snare 300 during loading of the cartridge to a distal tip of the deployment tool and preparing the suture snare for use. Parts that are similar to those described above will be given the same number. In particular, the deployment tool has an elongated tool shaft 204 that terminates in a distal tip 216 to which the cartridge 212 attaches.

Figure 16A:
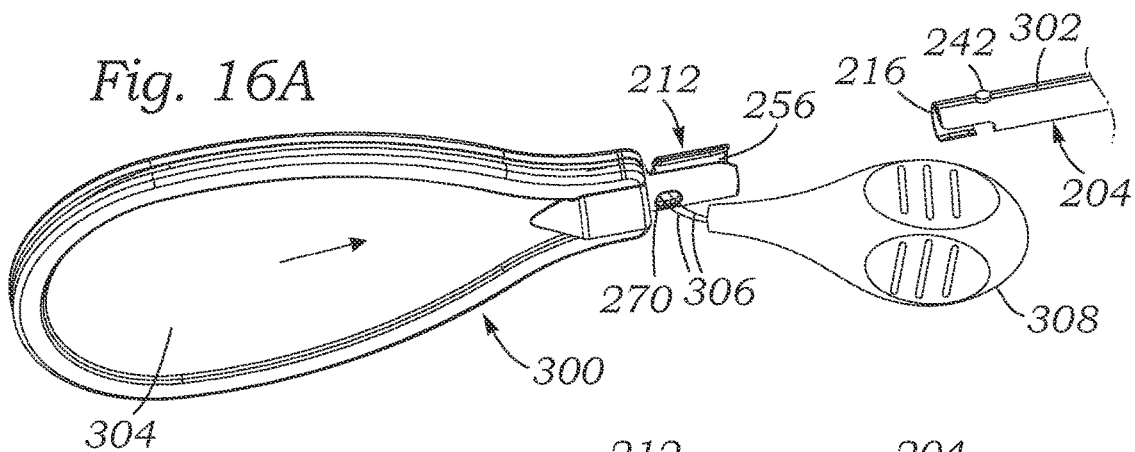
FIGS. 16A-16D illustrate several steps in loading an exemplary disposable fastener cartridge to a distal tip of the deployment tool and then preparing a suture snare for use.

In this embodiment, a marker line 302 is provided on the same side of the tool shaft 204 as the locking pin 242 and extends a short distance from the distal tip 216 in a proximal direction. This marker line 302 facilitates alignment of the axial slot 256 on the cartridge 212 with the locking pin 242. FIG. 16A shows relative displacement of the subassembly of the cartridge 212 and suture snare 300 toward the tool shaft 204. Eventually, as described above with respect to FIG. 13A, the locking pin 242 reaches the end of the axial slot 256.

Figure 16B:
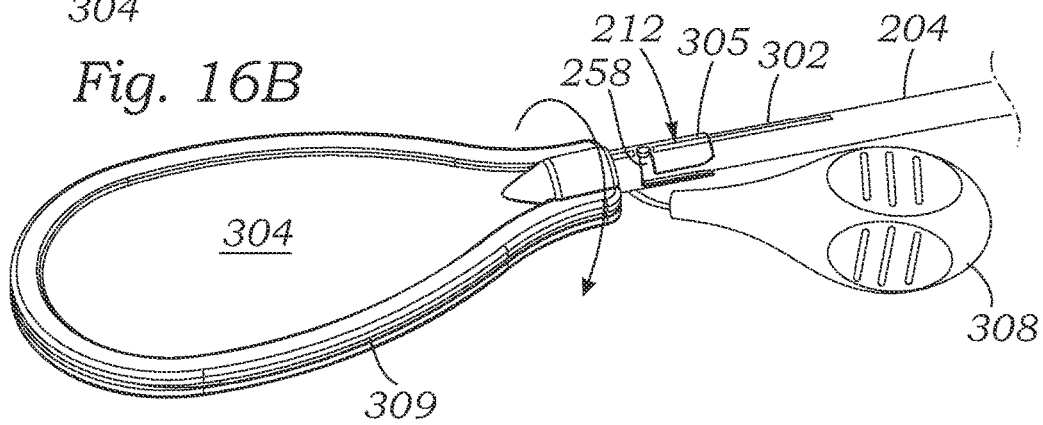

FIG. 16B shows 90° clockwise rotation of a placement grip/key 304 of the suture snare 300 relative to the tool shaft 204. This also rotates the fastener cartridge 212 relative to the shaft 204. As was explained above with respect to FIG. 13B, the locking pin 242 travels along the circumferential slot 258 on the cartridge 212 until it reaches and snaps into the lockout 260 (best seen in FIG. 12A). An additional indicator of complete engagement is the alignment of a second marker line 305 on the cartridge 212 with the marker line 302 on the shaft 204. At the same time, the circumferential portion 248a of the L-shaped slot 246 on the shaft 204 (see FIG. 11E) accommodates two strands of a flexible snare wire 306 as the cartridge and shaft are relatively rotated.

The snare 300 comprises the key 304, wire 306, and a proximal handle 308 in the form of a bulb. The flexible wire 306 extends from the proximal handle 308 and loops around the placement grip/key 304, preferably being held within an outer groove 309 therein. The loop formed by the wire 306 is routed around the groove 309 in the placement grip/key 304 for shipping, storage and handling purposes and to prevent twisting or tangling of the loop.

Figure 16C:
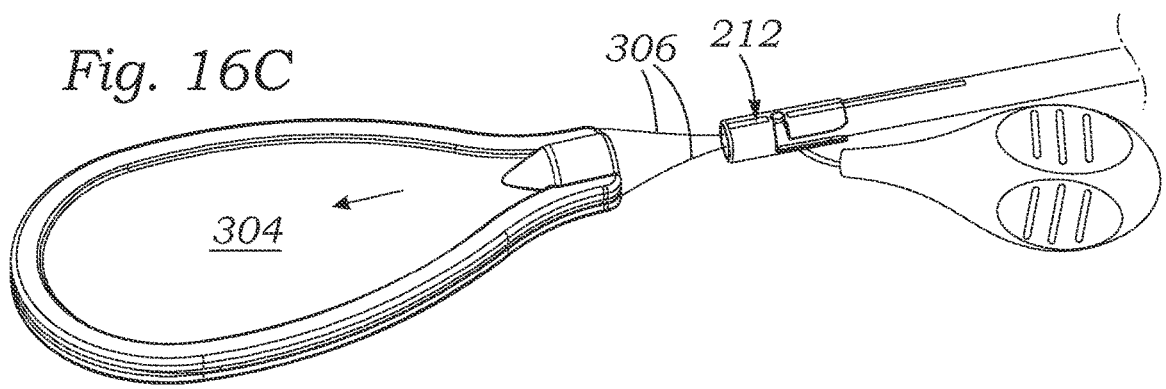
Figure 16D:
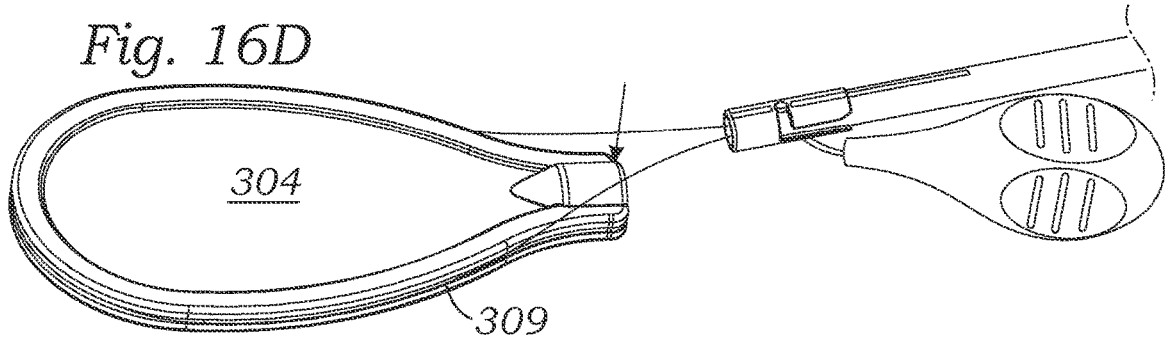

Subsequently, the user pulls the placement grip/key 304 axially away from the fastener cartridge 212 to create some separation therebetween, as seen in FIG. 16C. The two strands of the flexible wire 306 are thus exposed. At this point, the placement grip/key 304 can be removed from within the loop of the flexible wire 306 by pushing down on its proximal end, which is indicated by an arrow FIG. 16D. The suture fastener delivery system is now ready to use.

Figure 17A:
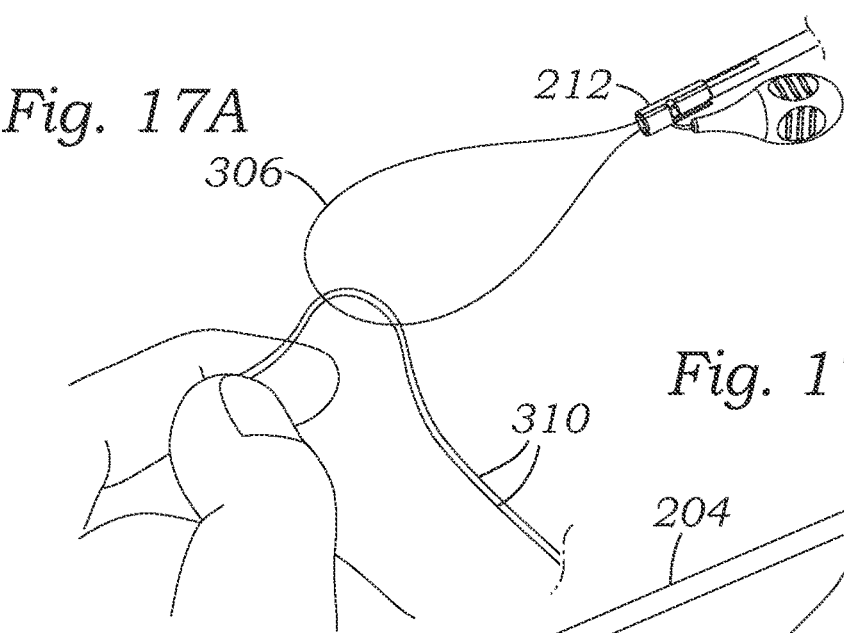
FIGS. 17A-17F show sequential steps in operation of the deployment tool and fastener cartridge during installation of a suture fastener on the proximal side of an annuloplasty ring.

FIGS. 17A-17F show sequential steps in operation of the deployment tool 200 and fastener cartridge 212 during installation of a suture fastener 250 on the proximal side of an annuloplasty ring, such as the annuloplasty ring 2 shown in FIG. 1. FIG. 17A shows a technician passing one or more strands of sutures 310 through the loop of the flexible wire 306. In the illustrated embodiment, there are two strands of sutures 310 which represent a pre-installed suture that has been passed through a native heart valve annulus, and then through a peripheral sewing edge of the annuloplasty ring 2. A minimum of 5 cm of the sutures 310 are passed through the snare loop 306 to ensure that they remain captured while pulled through the cartridge 212.

Figure 17B:
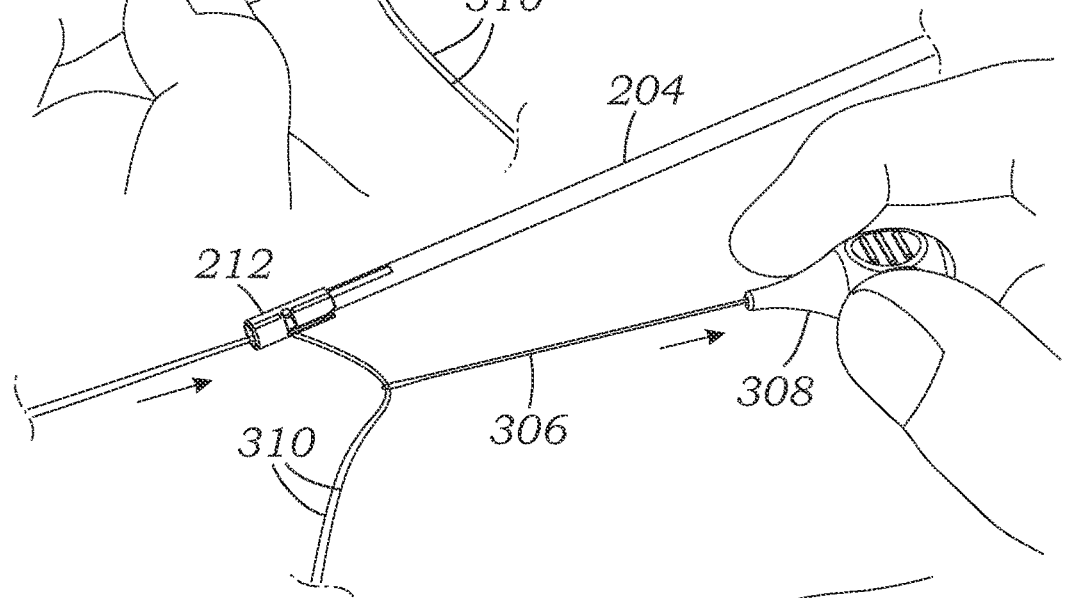
Figure 17C:
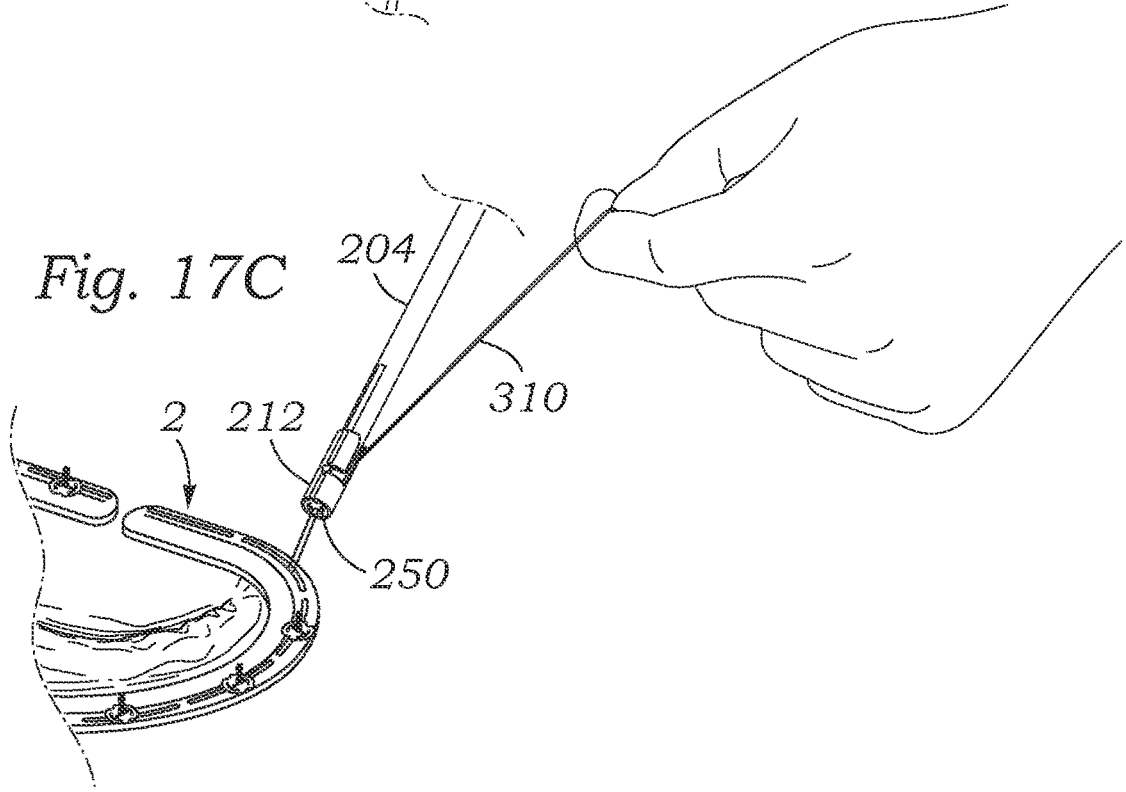

FIG. 17B illustrates the user pulling on the proximal handle 308 which in turn pulls the flexible wire loop 306 through the fastener cartridge 212, and also pulls the two strands of sutures 310 with it. The user then grasps the sutures 310 with one of his or her hands, as seen in FIG. 17C, to place the sutures in tension through the ring 2 to the annulus.

Figure 17D:
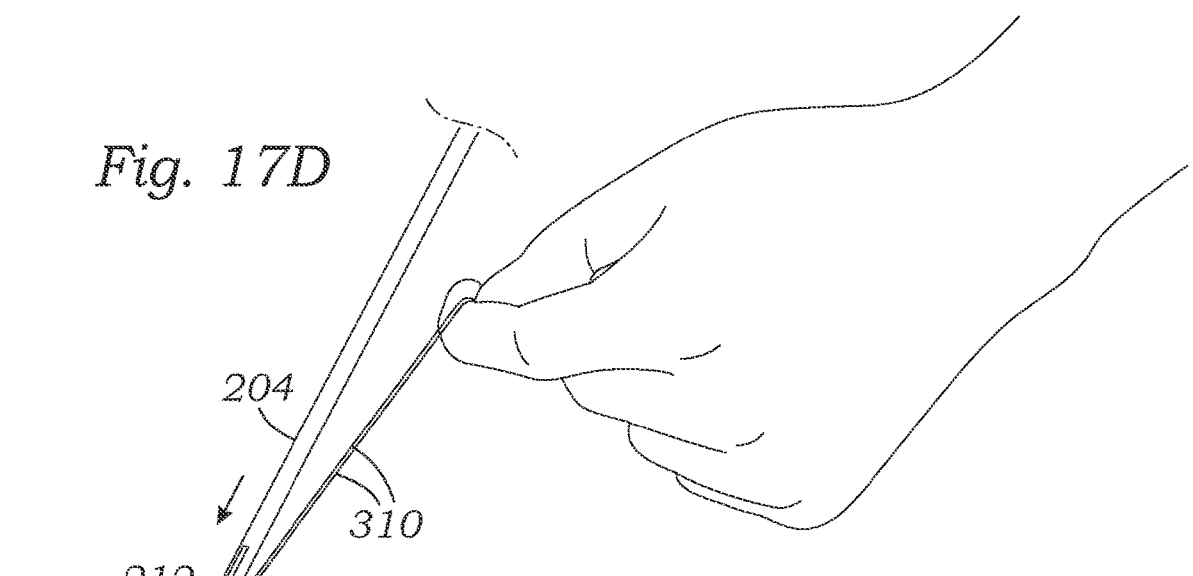

As seen in FIG. 17D, the user advances the distal tip of the shaft 204 having the cartridge 212 thereon down the sutures 310 to the target location on the annuloplasty ring 2. Only a portion of the annuloplasty ring 2 is shown indicating that several suture fasteners 250 are already installed.

Figure 17F:
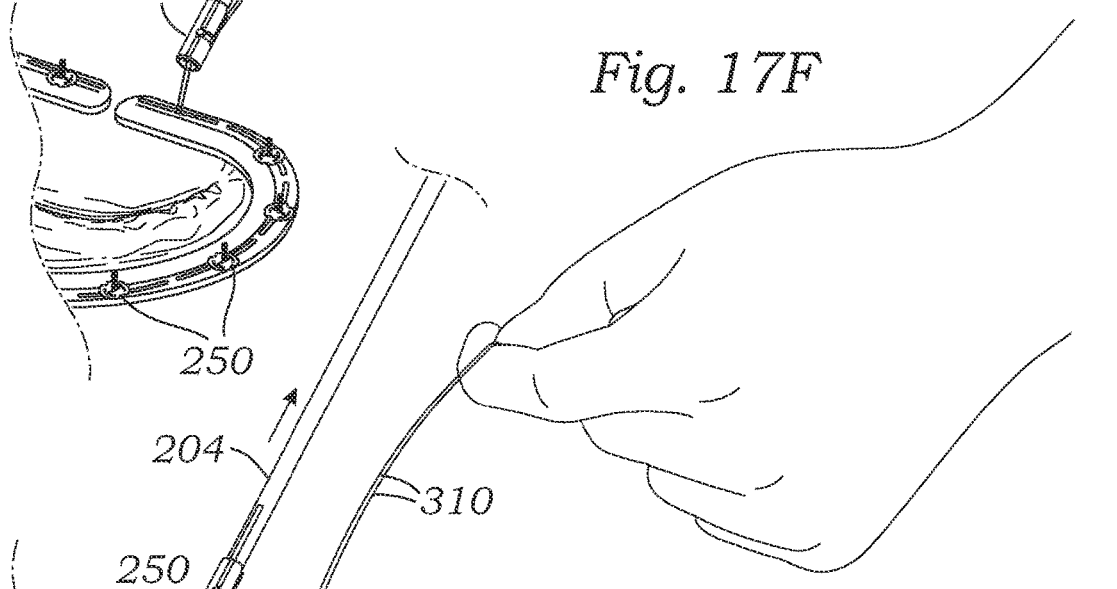
Figure 17E:
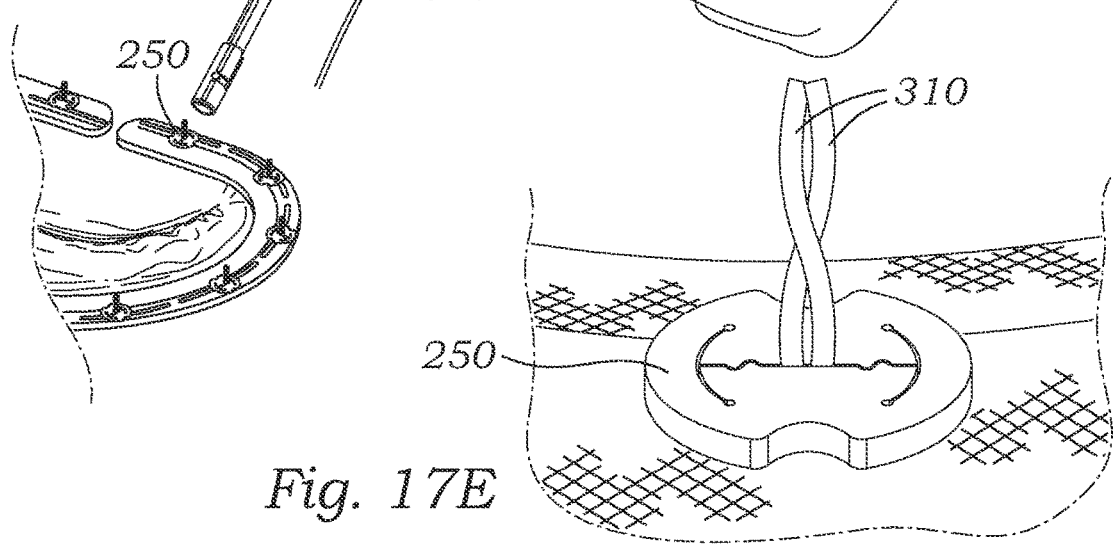

Finally, as seen in FIG. 17E, the user actuates the delivery tool such as by pulling the trigger actuator 206 as explained above, to deploy the suture fastener 250 and simultaneously cut the sutures 310. FIG. 17F is an enlargement of the installed suture fastener 250 showing short lengths of the sutures 310 remaining. At this stage, the fastener cartridge 212 will be removed from the shaft 204 to make way for another cartridge that has a suture fastener loaded therein.

FIGS. 18A-18C show the steps necessary for disengagement of a used fastener cartridge 212 from the distal tip of the deployment tool shaft 204. Disengagement is opposite from engagement, and involves rotating the cartridge 212 counterclockwise 90° and then pulling it axially free from the shaft 204. The deployment tool 200 is then ready for coupling with another fastener cartridge. Engagement of a disposable fastener cartridge 212 and suture snare 300 with the tool shaft 204, application of the suture fastener 250 to the target location, and removal of the spent cartridge 212 from the tool shaft 204 can be done in a very short amount of time. Cycle times of less than a minute are possible. This is significantly shorter than the time that it would take to tie off each of the sutures with a knot, especially in keyhole surgeries where space around the implant is limited.

FIG. 19 is a perspective cutaway view of the subassembly of the disposable fastener cartridge 212 and exemplary suture snare 300 of FIGS. 16A-16D. The fastener cartridge 212 has been described above, and will not be explained here other than to note that FIG. 20 is an exploded perspective view of the cartridge and a suture fastener 250.

As explained above, the suture snare 300 comprises the placement grip/key 304 connected via the flexible wire 306 to the proximal handle 308. The placement grip/key 304 and proximal handle 308 are desirably made of a relatively soft polymer such as an elastomer. A proximal end of the key 304 includes an enlarged annular sleeve 320 having an inner diameter that is sized approximately the same as the outer diameter of the fastener cartridge 212. The annular sleeve 320 can thus be pushed over the distal tip of the cartridge 212 and it will be held thereon by a close interference fit. The flexible wire 306 passes inward through the aligned ports 270, 244, as explained above, out through the suture fastener 250 at the distal end of the cartridge 212, backward between the sleeve 320 and the cartridge, and then into the peripheral groove 309 around the key. In a preferred embodiment, the flexible wire 306 is formed of an annealed stainless steel having a diameter of approximately 0.007 inches, and has sufficient flexibility to withstand kinking when routed in this manner.

While the disclosed technology has been described in its preferred embodiments, it is to be understood that the words which have been used are words of description and not of limitation. Therefore, changes may be made within the appended claims without departing from the true scope of the invention(s).

What is claimed is:

1. A system for securing a suture, comprising:
   a tool having a proximal portion and a distal shaft; and
   a subassembly configured to attach to of the distal shaft of the tool, the subassembly comprising:
      a cartridge configured to engage with the distal shaft of the tool;
      a suture fastener coupled to the cartridge, the suture fastener having a clamping structure holdable by the cartridge in an open position wherein a suture can pass through the clamping structure, and the clamping structure being reconfigurable to a closed position in which the clamping structure secures a suture passed therethrough; and
      a suture snare having a snare portion extending through the suture fastener, the suture snare being adapted to receive a suture and pull the suture proximally through the suture fastener;
   wherein the tool is configured to cause the suture fastener to deploy from the cartridge such that the suture fastener changes from the open position to the closed position to secure a suture extending through the suture fastener.

2. The system of claim 1, wherein the tool comprises a proximal handle with a trigger, and an ejector that extends through the distal shaft, and the ejector is longitudinally movable within the distal shaft upon actuation of the trigger, such that the ejector is configured to move the suture fastener to deploy the suture fastener from the cartridge.

3. The system of claim 2, wherein the ejector further includes a sharp edge, such that movement of the ejector severs a suture extending through the suture fastener and out of the cartridge.

4. The system of claim 1, wherein the suture fastener comprises a disk-shaped main body, and the clamping structure comprises at least one tab extending radially inwardly from the main body and being spring-biased toward the closed position where the at least one tab is aligned with the main body; and wherein at least one stop on the cartridge maintains the suture fastener in its open position by causing the at least one tab to be flexed out of alignment with the main body.

5. The system of claim 1, wherein the suture snare comprises the snare portion, a handle connected to the snare portion, and a grip having a peripheral groove for receiving and holding open a flexible loop of the snare portion, and wherein the grip is detachably coupled to a distal end of the cartridge.

6. The system of claim 1, wherein the cartridge is tubular and its proximal end includes a generally "L" shaped slot terminating in a circular lockout that receives a locking pin extending radially outwardly from the tool distal shaft, the cartridge engaging the distal shaft of the tool by axially advancing and then rotating thereover to position the locking pin in the circular lockout.

7. The system of claim 6, wherein the generally "L" shaped slot has an axially-extending portion and a circumferentially extending portion, and wherein the axially-extending portion aligns with a first port located on the cartridge, and the circumferential portion terminates in a second port located on the tool distal shaft, the first and second ports being aligned when the cartridge and tool distal shaft are fully engaged.

8. An assembly configured to be attached to a suture fastener tool, the assembly comprising:
   a cartridge configured to engage with the distal portion of the tool;
   a suture fastener coupled to the cartridge, the suture fastener having a clamping structure that is held by the cartridge in an open position wherein a suture can pass through the clamping structure, the clamping structure being movable toward a closed position in which the clamping structure contacts a suture passed therethrough; and
   a suture snare having a snare portion extending through the suture fastener in the open position, the snare portion being adapted to receive a suture and pull the suture proximally through the suture fastener.

9. The assembly of claim 8, wherein the suture fastener comprises a disk-shaped main body, and the clamping structure comprises at least one tab extending radially inwardly from the main body and being resiliently biased toward the closed position where the at least one tab is aligned with the main body; and wherein at least one stop on the cartridge maintains the suture fastener in its open position by causing the at least one tab to be flexed out of alignment with the main body.

10. The assembly of claim 8, wherein the suture snare comprises the snare portion, a handle connected to the snare portion, and a grip having a peripheral groove for receiving and holding open a flexible loop of the snare portion, and wherein the grip is detachably coupled to a distal end of the cartridge.

11. The assembly of claim 8, wherein the cartridge includes a metallic insert that forms at least one stop that maintains the suture fastener in the open position, the insert being positioned in a generally tubular polymeric body of the cartridge having an inner passageway, the stop being within the inner passageway.

12. The assembly of claim 8, wherein the cartridge is tubular and a sidewall of the cartridge includes a generally "L" shaped slot terminating in a circular lockout that is configured to receive a locking pin from a distal shaft of a suture fastener tool.

13. The assembly of claim 12, wherein the generally "L" shaped slot has an axially-extending portion that opens at a proximal end of the sidewall and a circumferentially extending portion that includes the circular lockout.

14. An assembly comprising:
 a cartridge configured to be coupled to a suture fastener tool;
 a suture fastener having a clamping structure that is held by the cartridge in an open position wherein a suture can pass through the clamping structure, the clamping structure being repositionable in a closed position in which the clamping structure clamps onto a suture passed therethrough; and
 an insert that comprises at least one stop that maintains the suture fastener in the open position, the insert being positioned adjacent the suture fastener such that the at least one stop is engaged with the clamping structure of the suture fastener.

15. The assembly of claim 14, wherein the cartridge comprises a polymeric material and the insert comprises a metallic material.

16. The assembly of claim 14, wherein the cartridge is tubular and a sidewall of the cartridge includes a generally "L" shaped slot terminating in a circular lockout that is configured to receive a locking pin from a distal shaft of a suture fastener tool.

17. The assembly of claim 16, wherein the generally "L" shaped slot has an axially-extending portion that opens at a proximal end of the sidewall and a circumferentially extending portion that includes the circular lockout.

18. The assembly of claim 14, wherein the suture fastener comprises a disk-shaped main body, and the clamping structure comprises at least one tab extending radially inwardly from the main body and being resiliently biased toward the closed position where the at least one tab is aligned with the main body; and wherein the at least one stop maintains the suture fastener in its open position by causing the at least one tab to be flexed out of alignment with the main body.

19. The assembly of claim 14, wherein the cartridge comprises a radial opening positioned proximal to the suture fastener, the radial opening configured to allow a suture snare to extend radial into the cartridge, axially through the suture fastener, and out of the distal portion of the cartridge.

20. The assembly of claim 14, wherein the insert comprises an annular body positioned proximal to the suture fastener, and the insert comprises two spaced apart stops that extend distally from the annular body through the clamping structure to maintain the suture fastener in the open position.

* * * * *